(12) United States Patent
Stefan et al.

(10) Patent No.: US 8,882,750 B2
(45) Date of Patent: Nov. 11, 2014

(54) TOOL FOR A MICRO-INVASIVE SURGICAL INSTRUMENT

(75) Inventors: Jochen Stefan, Wald (DE); Daniel Kaercher, Radolfzell (DE); Uwe Bacher, Tuttlingen (DE)

(73) Assignee: Karl Storz GmbH & Co. KG (DE)

( * ) Notice: Subject to any disclaimer, the term of this patent is extended or adjusted under 35 U.S.C. 154(b) by 267 days.

(21) Appl. No.: 13/444,578

(22) Filed: Apr. 11, 2012

(65) Prior Publication Data

US 2012/0259319 A1    Oct. 11, 2012

(30) Foreign Application Priority Data

Apr. 11, 2011    (DE) .......................... 10 2011 007 122

(51) Int. Cl.
*A61B 17/00* (2006.01)
*A61B 17/29* (2006.01)

(52) U.S. Cl.
CPC ......... *A61B 17/29* (2013.01); *A61B 2017/0046* (2013.01); *A61B 2017/294* (2013.01); *A61B 2017/2931* (2013.01); *A61B 2017/00477* (2013.01); *A61B 2017/2939* (2013.01); *A61B 2017/2929* (2013.01); *A61B 2017/2945* (2013.01)
USPC ............................. 606/1; 606/205

(58) Field of Classification Search
CPC ..................... A61B 17/29; A61B 2017/00466; A61B 2017/00477; A61B 2017/2929; A61B 2017/2931; A61B 2017/2939; A61B 2017/294; A61B 2017/2945
USPC ............................. 606/1, 205–209
See application file for complete search history.

(56) References Cited

U.S. PATENT DOCUMENTS

| 5,308,358 | A | * | 5/1994 | Bond et al. ..................... 606/205 |
| 5,507,297 | A | * | 4/1996 | Slater et al. .................... 600/564 |
| 5,527,339 | A | * | 6/1996 | Koscher et al. ............... 606/205 |
| 5,603,723 | A | * | 2/1997 | Aranyi et al. ................. 606/205 |
| 5,607,449 | A | * | 3/1997 | Tontarra ........................ 606/205 |

(Continued)

FOREIGN PATENT DOCUMENTS

| DE | 9317535 U1 | 1/1994 |
| DE | 4332497 A1 | 3/1995 |

(Continued)

OTHER PUBLICATIONS

German Search Report; Application No. DE 102011007122.9; Issued: Feb. 2, 2012; 5 pages.

*Primary Examiner* — William Thomson
*Assistant Examiner* — Boniface N Nganga
(74) *Attorney, Agent, or Firm* — St. Onge Steward Johnston & Reens LLC

(57) ABSTRACT

A tool, which is detachably coupleable with a shaft for a micro-invasive surgical instrument, includes an articulated device on which a jaw member or other active device is affixed, a connecting component that is rotatably connected with the articulated device and that includes a coupling device for detachable coupling with a distal end of a shaft, a transmission rod to transmit at least either a force or torque from one proximal end of a shaft detachably coupled with the tool to the jaw member or other active device, and a locking device that is coupled with the transmission rod in such a way that the locking device can be rotated with respect to the transmission rod but not slid axially, so that the locking device is mounted in the connecting component in such a way that it can be axially slid but not rotated in relation to the connecting component.

14 Claims, 9 Drawing Sheets

(56) References Cited

U.S. PATENT DOCUMENTS

| | | | |
|---|---|---|---|
| 5,817,128 A * | 10/1998 | Storz | 606/205 |
| 5,893,875 A * | 4/1999 | O'Connor et al. | 606/205 |
| 6,126,359 A * | 10/2000 | Dittrich et al. | 403/349 |
| 6,340,365 B2 * | 1/2002 | Dittrich et al. | 606/205 |
| 2004/0127890 A1* | 7/2004 | Bacher | 606/1 |
| 2007/0073247 A1* | 3/2007 | Ewaschuk | 604/264 |
| 2008/0004656 A1* | 1/2008 | Livneh | 606/205 |
| 2008/0015634 A1* | 1/2008 | Summerer | 606/208 |
| 2008/0046001 A1* | 2/2008 | Renger et al. | 606/205 |
| 2008/0275441 A1* | 11/2008 | Aue | 606/41 |

FOREIGN PATENT DOCUMENTS

| | | |
|---|---|---|
| DE | 19707373 C1 | 2/1998 |
| DE | 102006038516 A1 | 2/2008 |
| DE | 102008015418 A1 | 9/2009 |
| DE | 102008052623 A1 | 4/2010 |
| EP | 1889579 A2 | 2/2008 |

* cited by examiner

TOOL FOR A MICRO-INVASIVE SURGICAL INSTRUMENT

CROSS-REFERENCE TO RELATED APPLICATIONS

The present application claims priority of German patent application No. 10 2011 007 122.9 filed on Apr. 11, 2011, the content of which is incorporated herein by reference.

FIELD OF THE INVENTION

The present invention relates to a tool for a micro-invasive surgical instrument, a micro-invasive surgical instrument and thus, in particular, characteristics for mechanical coupling of the tool with a distal end of a shaft.

BACKGROUND OF THE INVENTION

Many micro-invasive surgical instruments include a long, thin shaft, a tool on the distal end of the shaft and a handling device on the proximal end of the shaft. The tool includes, for example, a grasping, dissecting, biopsy or other forceps, a scissors or a needle holder with at least two straight or curved clamps, cutting edges or other jaw members of which at least one is movable. Alternatively, the tool includes another active device, for example a manipulator with a finger or a finger-shaped device or an electrode in hook form or other shape. The shaft contains (at least) one transmission rod, which as a rule is mounted in a closed channel in the interior of the shaft. The handling device includes one or more actuation devices that can move with respect to one another, for example two gripping parts, that medical staff can move in relation to one another with one hand. The proximal end and the distal end of the transmission rod are coupled with the actuation device or with the tool in such a way that a force exerted by medical staff onto the actuation devices or a relative movement of the actuation devices caused by medical staff can be transmitted to the tool, for example to move clamps toward one another or to press them together.

In using a micro-invasive surgical instrument of this type, the tool and a part of the shaft are inserted into a natural or artificial cavity in the patient's body, for example through a natural or artificial bodily opening. The development of micro-invasive surgical techniques tends toward using constantly smaller and, especially, fewer means of access. For example, in order to be able to work with an endoscope and two instruments in laparoscopic surgery by way of a single trocar, instruments with curved shafts can be used. An instrument with a curved shaft, however, cannot always be easily rotated around its longitudinal axis inside the access way in order to modify the orientation of the tool at its distal end.

In patent DE 10 2006 038 516 A1, a tubular medical instrument is described in which a tool 5, a shaft 3 and a handle 2 can be separated from one another for cleaning.

Patent DE 10 2008 015 418 A1 discloses a medical instrument with a curved shaft. A jaw member is detachably connected with a shaft by means of a bayonet lock. In connected position, the jaw member can be rotated with respect to the shaft. The shaft is detachably connected with a handle. The curved shaft can be rotated with respect to the handle by means of a hand wheel that is connected with an external shaft tube in torque-proof manner. An inside tube is connected to the handle with an additional hand wheel. The instrument can be configured as a unipolar or bipolar HF instrument.

Patent DE 10 2008 052 623 A1 discloses a surgical instrument with a jaw unit, a shaft and a gripping unit. The jaw unit is detachably affixed to the end of a shaft tube of the shaft and can rotate with respect to it.

To allow easy, thorough cleaning of the instrument, the tool, shaft and handling device of a micro-invasive surgical instrument, without use of auxiliary means, ought to be separable from one another and capable of being combined or coupled with one another. It is known, for example, from DE 10 2006 038 516 A1 how to configure the tool and the distal end of the shaft in such a way that the tool can be assembled and disassembled in a fully open assembled position. However, a few aspects both of the coupling of the tool with the shaft and of the coupling of the shaft with the handling device have not been sufficiently satisfactorily resolved to date, especially concerning the ability of the tool to turn or rotate with respect to the shaft when in coupled state.

SUMMARY OF THE INVENTION

An object of the present invention consists in providing an improved tool for a micro-invasive surgical instrument and an improved micro-invasive surgical instrument.

This object is fulfilled through the content of the independent claims.

Refinements are indicated in the dependent claims.

A tool that can be mechanically coupled with a distal end of a shaft for a micro-invasive surgical instrument includes an articulated device to which a jaw member or other active device is attached, a connecting component that is mechanically connected in rotatable manner with the articulated device and comprises a coupling device for detachable mechanical coupling with a distal end of a shaft, a transmission rod to transmit at least either a force or torque from a proximal end of a shaft that is detachably mechanically coupled with the tool to the jaw member or other active device, and a locking device that is mechanically coupled with the transmission rod in such a way that the locking device can be rotated with respect to the transmission rod but cannot be slid axially, such that the locking device is mechanically stored in the connecting component in such a way that the locking device can slide axially, but cannot rotate, with respect to the connecting component.

The tool includes in particular a grasping, dissecting, biopsy or other forceps, a scissors or a needle holder with at least two straight or curved clamps, cutting edges or other jaw members, at least one of which is movable. The jaw member can accordingly be configured as a clamp or cutting edge. The tool can include two or more jaw members that can be moved symmetrically and synchronously. Alternatively, the tool can include, for example, a jaw member that is rigidly connected with the articulated device and one that is attached jointedly to the articulated device. The articulated device, with respect to the jointed or rigid attachment of jaw members to the articulated device, can be configured in similar manner as is familiar with fork devices in conventional tools for micro-invasive surgical instruments. Alternatively, the tool includes another active device, for example a manipulator with a finger or finger-shaped device or an electrode in hook form or other shape.

The connecting component is, for example, in sheath form or essentially in sheath form and can be composed of one or more elements. The longitudinal axis of the connecting component, of a shaft, transmission rod or other proximal end of a shaft or transmission rod, is intended to mean, in particular, the axis with which the particular object is rotation-symmetrical or essentially rotation-symmetrical. In the case of a curved shaft or a pliable transmission rod, these terms refer particularly to their ends, which as a rule are at least partially straight or not curved.

The connecting component can have a shape that markedly diverges from rotation symmetry with respect to an axis or from axial symmetry. Clear divergences can be present particularly on the coupling device. Nevertheless, however, the connecting component has particular characteristics that are of rotation-symmetrical or essentially rotation-symmetrical configuration. In particular, the connecting component, at its distal end or close to its distal end, has traits of rotation symmetry to its longitudinal axis, by which it is rotatably mechanically connected with the articulated device.

Therefore the connecting component, on the one hand, can be detachably mechanically coupled with the distal end of a shaft by means of its coupling device, and on the other hand is connected with the articulated device so that it can rotate around its longitudinal axis. Thereby the connecting component makes it possible for it to be mounted on and disassembled from a distal end of a shaft, and simultaneously for the articulated device and especially the jaw members or other active devices to rotate around a longitudinal axis of the tool and/or around a longitudinal axis of the distal end of a shaft.

Particularly when the tool is intended for detachable mechanical coupling with a curved shaft, the transmission rod is pliable in order to make it possible to rotate the transmission rod in the shaft around its longitudinal axis and to slide the transmission rod axially, even with varying curvature of the shaft. The locking device, in particular, can rotate around the local longitudinal axis of the transmission rod. The characteristic whereby the locking device cannot slide axially with respect to the transmission rod also means that the locking device essentially cannot slide axially with respect to the transmission rod. A slight capacity for axial sliding because of mechanical play cannot be ruled out.

Because the locking device can rotate with respect to the transmission rod and because the locking device is fed in the grove or slot, the locking function of the locking device can be independent of the orientation of the transmission rod with respect to a rotation around its longitudinal axis. Instead, the effect of the locking device depends exclusively on the position of the transmission rod with respect to sliding in the longitudinal direction.

The transmission rod comprises, in particular, an electrically conducting material and is electrically conductively connected with a jaw member or other active device of the tool. In this case, electric voltage, current and electric power can be transmitted via the transmission rod to the jaw member or other active device. The tool can thus be used, for example, for HF coagulation.

The coupling device is configured in particular as a bayonet coupling.

With a tool as described here, the locking device can be slid, in particular, in the axial direction between an installation position and a working position, such that with the locking device in the installation position, the connecting component can be connected with a distal end of a shaft and is detachable from it, and such that with the locking device in the working position, a mechanical connection of the tool with a distal end of a shaft is locked.

The locking device particularly comprises several working positions or one range of working positions, referred to hereinafter as the working range. The installation position of the locking device is situated, in particular, at a distance in the distal direction from the working position or working range. The locking device is slidable, in particular, in linear manner, parallel to the longitudinal axis of the tool. In addition, the locking device can be rotatable. In particular, the locking device is rotatable together with the connecting component in relation to the articulated device of the tool.

With a locking device that can slide in the axial direction, a reliable locking of the tool on the distal end of a shaft becomes possible, in particular with a bayonet coupling.

The locking device, in particular, engages in a groove or slot on the coupling device of the connecting component that is configured as a bayonet coupling.

With a tool as described here, the locking device particularly includes a ring-shaped portion that engages in a surrounding groove on the transmission rod.

With a tool with a transmission rod as described here, the locking device at least either comprises an electrically insulating material or is electrically insulated from the transmission rod.

An electrical insulation of the locking device from the transmission rod or an electrically insulating property of the locking device itself makes it possible to produce the tool as electrically bipolar, such that, for example, a first jaw member can be connected via the transmission rod with a first pole of a power source and a second jaw member can be connected via the bayonet coupling and a shaft with a second pole of the power source.

With a tool as described here, the articulated device particularly comprises an electrically insulating material, such that the tool further includes an electrically conducting conductor component that is positioned at least partly in the articulated device for electrical contacting of a jaw member or other active device that is electrically insulated from the transmission rod.

The electrically conducting conductor component is, in particular, elastically configured, for example on the basis of a helical portion. Owing to this elasticity, the electrically conducting conductor component makes it possible to contact a jaw member that can pivot with respect to the articulated device or another active device that can pivot with respect to the articulated device. The electrically conducting conductor component is connected in particular with the aforementioned contact component in electrically conducting manner. This allows high voltage and a corresponding current to be conducted by a bayonet lock between the shaft and tool, the connecting component, the supporting sheath, the contact component and the electrically conductive component to one of the jaw members or to another active device of the tool. If the second or additional jaw member or a second or additional active device of the tool is electrically contacted via the transmission rod, the tool can be used as a bipolar tool for HF coagulation.

The coupling device is particularly configured as a bayonet coupling with a bracket, such that the locking device includes a convex portion and such that the bracket and the convex portion are set apart at a distance on the locking device in axial direction and in the peripheral direction and are configured to engage in a groove or slot on a distal end of a shaft.

The bayonet coupling includes in particular two or more symmetrically positioned brackets, which are each configured to engage in a groove or a slot on a distal end of a shaft. The bracket or brackets are, in particular, each configured to engage in an L-shaped groove or an L-shaped slot with a portion extending in the axial direction and with a portion extending in the peripheral direction. The bracket and the convex portion on the locking device—one bracket each and one convex portion, in the case of several brackets and several convex portions—are configured and arranged to engage in one and the same groove or one and the same slot.

Because of the rotatability of the locking device with respect to the transmission rod, installation and disassembly of the tool and of a shaft become possible, similarly as with a conventional bayonet coupling. Intuitive handling by medical staff becomes possible or is made easier. In addition, the rotatability of the transmission rod with respect to the locking device allows transmission of torque and of a rotary movement to the tool by means of the transmission rod.

With a tool as described here, with a bracket set at a distance from a convex portion of the locking device in axial direction and in peripheral direction and with a locking device that can slide between an assembly position and a working position, the locking device is particularly configured and positioned to hamper rotation of the coupling device with respect to the distal end of the shaft in the working position by engaging in a portion of a groove or slot extending in axial direction at a distal end of a shaft.

Because of the hampering of the rotation of the coupling device in relation to the distal end of the shaft, the bracket of the bayonet coupling of the tool is, in particular, held in a portion of the groove or of the slot extending in the peripheral direction at the distal end of the shaft.

The coupling device configured as a bayonet coupling particularly includes (and in particular instead of one or more brackets) a groove or slot or two or more grooves or slots. Said groove or grooves or slot or slots are, in particular, bent at an angle with a portion extending parallel or essentially parallel to the longitudinal axis and a portion extending in peripheral direction or essentially in peripheral direction.

The locking device comprises, in particular, several working positions or a range of working positions, referred to hereinafter as working range. The installation position of the locking device is situated, in particular, at a distance in the distal direction from the working position or working range. The locking device, in particular, can slide linearly parallel to the longitudinal axis of the tool. In addition, the locking device can be rotatable. In particular, the locking device together with the connecting component can rotate with respect to the articulated device of the tool.

With a locking device that can slide in axial direction and thus, in particular, perpendicular to a portion of a groove or slot of a bayonet coupling extending in the peripheral direction, a reliable locking of the tool on the distal end of a shaft becomes possible.

The locking device, in particular, engages in a groove or slot on the coupling device of the tool that is configured as a bayonet coupling.

The groove or slot is provided in order to receive a bracket or a claw on the distal end of a shaft that is to be connected with the tool. Because of an especially axial sliding of the locking device inside the groove or slot, a mechanical coupling between the tool and a distal end of a shaft can be locked.

The groove or slot particularly comprises a T-shaped form with an axial portion that extends in axial direction and a peripheral portion that extends in the peripheral direction, whereby a proximal area of the axial portion is positioned proximally from an outlet of the peripheral portion into the axial portion, whereby a distal area of the axial portion is positioned distally from an outlet of the peripheral portion into the axial portion, whereby the locking device in the installation position engages only in the distal area of the axial portion of the groove or slot, so that a bracket on a shaft that is to be connected with the tool can be inserted into the peripheral portion of the groove or slot through the proximal area of the axial portion, and whereby the locking device in the working position at least partly blocks the outlet of the peripheral portion of the groove or slot into the axial portion, so that a bracket positioned in the peripheral portion of the groove or slot is held in the peripheral portion by the locking device.

The T-shaped form of the groove or slot also includes in particular an essentially T-shaped form in which the axial portion extends essentially in axial direction and/or the peripheral portion extend essentially in peripheral direction, whereby the angles between the axial portion and the peripheral portion depart from 90 degrees, to lie for example within a range from 70 to 110 degrees or from 80 to 100 degrees. In addition, both the axial portion and the peripheral portion of the groove or slot have a curved shape in each case. For example, installation and disassembly can be simplified by an arched shape of the axial portion and/or by an arched shape of the peripheral portion.

The described T-shaped or essentially T-shaped form of the groove or slot, which is provided for a bracket on the distal end of a shaft that is to be mechanically coupled with the tool, and the engagement of the locking device in an axial portion can make possible a simple and robust locking of the mechanical coupling between tool and shaft. Construction and production of the tool can, in particular, be simplified by having the groove or slot fulfill two functions simultaneously, namely form-locking with a bracket on the distal end of a shaft and guidance of the locking device. The bayonet coupling can be configured in such a way that it can be handled by medical staff, for example, without any special readjustment, exactly like any conventional bayonet coupling.

With a tool as described here, the jaw member in particular is electrically insulated from another jaw member, whereby the other jaw member is connected in electrically conductive manner with a contact component that is mechanically rigidly connected with the articulated device, whereby a proximal front surface of the contact component is contiguous with a contact surface that is mechanically rigidly connected with the connecting component, whereby the contact component and the contact surface that is mechanically rigidly connected with the connecting component are provided and configured to form an electrically conductive connection between a shaft connected with the tool and the other jaw member.

The jaw member and the other jaw member of the tool are configured in particular to be connected with one pole each of an electric voltage, current or power source. The proximal front surface of the contact component and the contact surface mechanically rigidly connected with the connecting component are each, in particular, of annular shape. The proximal front surface of the contact component and the contact surface mechanically rigidly connected with the connecting component are each, in particular, flat.

An electrically conductive connection of the other jaw member with the shaft is possible via the contact surface mechanically rigidly connected with the connecting component and the proximal front surface of the contact component, regardless of the position of the tool in relation to the connecting component and to the shaft. In particular, it can be simple and economical to produce an annular and flat configuration, in each case, of the proximal front surface of the contact component and of the contact surface mechanically rigidly connected with the connecting component. When the jaw members are moved proximally in the direction toward their closed positions by a tractive force acting on the transmission rod, the proximal front surface of the contact component is pressed against the contact surface that is mechanically rigidly connected with the connecting component. Therefore the electrical contact between the contact component and the contact surface mechanically rigidly connected with the connecting component exists at least when the jaw members are closed against a mechanical resistance.

With a tool as described here, the connecting component can comprise close to its distal end a collar that is interrupted by several essentially axial slots and that engages in a corresponding groove on the articulated device, whereby the tool in addition comprises a support device that is configured to hamper a radial reshaping of the collar and to hold the collar in the groove.

The collar and groove, in terms of their shape and dimensions, are particularly configured in such a way that they make possible a low-friction and low-play rotation of the articulated device in relation to the connecting component. The collar in particular extends radially outward in order to engage radially from inside in the corresponding surrounding groove that is open radially toward the inside on the articulated device. The support device in this case is positioned inside the connecting component, in particular opposite the collar in the radial direction. The support device is particularly a supporting sheath in the form of a ring or tube whose outside is contiguous with an inward side of the connecting component and thus prevents a radial reshaping of the collar. Alternatively, the collar on the connecting component can engage from outside in a surrounding groove, open to the outside, on the articulated device, whereby the support device, for example, is a supporting sheath that surrounds the connecting component close to the collar.

A collar on the connecting component that engages in a groove on the articulated device can make possible a form-locking, reliable and robust connection between the articulated device and the connecting component. The axial slots can make it possible to manufacture the tool in simple manner so that the connecting component is elastically reshaped in the area of the collar while in the axial direction it is inserted into the articulated device or is pulled over the articulated device. Thereafter the elastic reshaping of the collar can be halted by the supporting sheath or another support device in order to connect the connecting component and the articulated device in a durable form-locking manner.

A tool as described here, in which the support device is configured as a supporting sheath, can also include a contact component with a contact surface that is contiguous with the supporting sheath, whereby the contact component is configured and positioned to be rotatable together with the articulated device in relation to the connecting component.

The contact component is, for example, sheath-shaped or tubular with longitudinal slots. The contact component is elastically reshaped by the supporting sheath by means of a slight excess, in order to generate sufficient contact force between the contact component and the supporting sheath for a reliable electrical contact.

The supporting sheath thus combines two functions, namely that of mechanically supporting the collar on the connecting component and that of electrical contacting, thereby permitting a particularly simple and compact structure.

With a tool as described here, the jaw member is, in particular, curved.

In particular, the jaw includes two or more curved jaw members. Provided that a curved jaw member can pivot around a pivot axis, it is curved in particular in a plane perpendicular to the pivot axis or in a plane parallel to the pivot axis or in both directions.

Clamps, cutting edges or other jaw members of micro-invasive surgical instruments that are curved in arched or even screw-like shape are especially suited for a few applications. However, in using a tool with two curved jaw members, contrary to a tool with two equal or similar, straight or essentially straight jaw members, a rotation by more than 90 degrees (up to 180 degrees) can be required in order to align the tool correctly in relation to an object. It can therefore be particularly advantageous if a tool with one or more curved jaw members is rotatable around a longitudinal axis of a shaft of a tool.

A micro-invasive surgical instrument includes a shaft having a proximal end that can be coupled or is coupled with a handling device and having a distal end and a tool, as described here, that can be detachably mechanically coupled with the distal end of the shaft.

The shaft of the micro-invasive surgical instrument can be straight or curved, rigid or flexible. In the case of a curved or flexible shaft, a transmission rod is provided, in particular, that is pliable at least in some parts. The tool particularly includes a grasping, dissecting, biopsy or other type of forceps, a scissors or a needle holder with at least two straight or curved clamps, cutting edges or other jaw members, at least one of which is movable. Alternatively, the tool can include another active device, for example a manipulator with a finger or a finger-shaped device or an electrode in hooked shape or some other form. The transmission rod is particularly configured to transmit a tractive and/or pushing force to the tool on the distal end of the shaft.

With the characteristics and properties of the tool and corresponding characteristics and properties of the shaft and transmission rod, a simple, rapid and reliable installation and efficient use of the micro-invasive surgical instrument are possible.

The transmission rod is particularly configured for transmitting torque from the handling device to a tool on the distal end of the shaft. The transmission rod is thus rigid or inelastic, particularly concerning pressure or tractive impacts in the longitudinal direction and concerning torsion. The transmission rod can simultaneously be pliable, particularly in the case of a shaft that is curved at least in parts.

The detachable connection between the tool and shaft can improve, or in fact altogether make possible, the cleaning of the instrument. The locking of the tool on the distal end of the shaft when the position of the rod coupling coupled with the proximal end of the transmission rod is situated in the predetermined working range, can allow the instrument to be completely dismantled, owing entirely to the release of the locking of the shaft on the handling device. This can markedly simplify or improve the handling of the instrument, especially its dismantling and reassembly.

With a micro-invasive surgical instrument as described here, the distal end of the shaft can comprise a bayonet coupling area with an L-shaped groove or an L-shaped slot.

The L-shaped groove or L-shaped slot particularly includes a portion extending in the axial direction and a portion extending in the peripheral direction.

BRIEF DESCRIPTION OF THE DRAWINGS

Embodiments are presented in greater detail hereinafter with reference to the attached drawings, which are as follows.

DETAILED DESCRIPTION OF THE INVENTION

Figure 1:
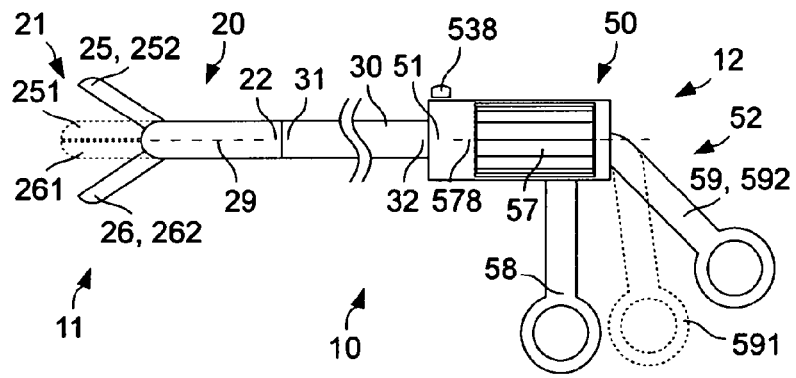
FIG. 1 shows a schematic depiction of a micro-invasive surgical instrument.

FIG. 1 shows a schematic depiction of a micro-invasive surgical instrument 10 with a distal end 11 and a proximal end 12. The micro-invasive surgical instrument 10 includes a tool 20, a shaft 30 and a handling device 50. On the distal end 21 the tool 20 comprises a first movable jaw member 25 and a second movable jaw member 26. The jaw members 25, 26 are shown in FIG. 1 in firm outline in open positions 252, 262 and in dotted lines in closed positions 251, 261. The jaw members 25, 26 can each be straight or essentially straight or can be curved in the direction perpendicular to the plane of projection of FIG. 1 and/or—contrary to the depiction in FIG. 1—in the plane of projection of FIG. 1.

The proximal end 22 of the tool 20 is detachably mechanically coupled with a distal end 31 of the shaft 30. The shaft 30 is shown strongly foreshortened in FIG. 1 and straight for the sake of simplicity. Contrary to the depiction in FIG. 1, the shaft 30 can be level or spatially curved. With a shaft 30 that is within a plane or—even more advantageous for a few applications—spatially curved in shape, the micro-invasive surgical instrument 10 can be suited especially for surgical procedures in which the endoscope and one or more instruments are inserted simultaneously into a body cavity through a single access way.

The proximal end 32 of the shaft 30 is detachably mechanically coupled with the distal end 51 of the handling device 50. The handling device 50 comprises a rotary wheel 57, a first gripping member 58 and a second gripping member 59 for handling the micro-invasive surgical instrument 10. The rotary wheel 57 is provided to control a rotation of the tool 20, in particular the jaw members 25, 26, around a longitudinal axis 29. In the example shown in FIG. 1, the rotary wheel 57 can rotate around an axis 578 that is simultaneously the longitudinal axis of the shaft 30 on its proximal end 32. Alternatively, the axis 578 can be parallel to the longitudinal axis of the shaft 30 on its proximal end 32. In addition, the rotary wheel 57 comprises a surface structure that allows reliable operation or actuation even with gloves, for example the indicated pin in the axial direction. The gripping members 58, 59 in particular—contrary to the strongly stylized shape shown in FIG. 1—are positioned and formed in such a way that medical staff can grip and move the two gripping members 58, 59 in relation to one another with one hand without little fatigue.

At least one of the two gripping members 58, 59 is movable in relation to the other components of the handling device 50. In the example shown in FIG. 1, the first gripping member 58 is rigidly positioned and the second gripping member 59 is movably positioned. The second gripping member 59, in particular, is movable between the first working position 591 shown in dotted lines in FIG. 1 and a second working position 592 indicated in firm lines in FIG. 1. The second gripping member 59 of the handling device 50 is mechanically coupled with the jaw members 25, 26 of the tool 20 in such a way that the jaw members 25, 26 happen to be in their closed positions 251, 261 when the second gripping member assumes its first working position 591, and that the jaw members 25, 26 happen to be in their open positions 252, 262 when the second gripping member 59 assumes its second working position 592.

Figure 2:
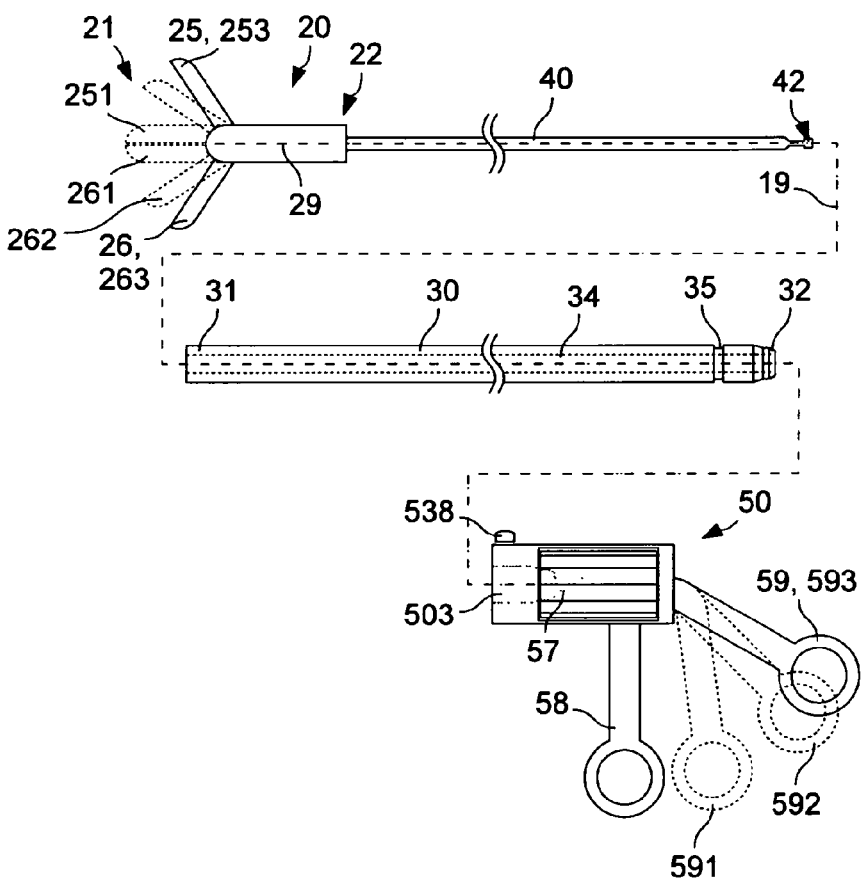
FIG. 2 shows a schematic depiction of the micro-invasive surgical instrument from FIG. 1 in dismantled form.

FIG. 2 shows a schematic depiction of components of the micro-invasive surgical instrument 10 described above with reference to FIG. 1, which can be installed and/or assembled to form an instrument without use of a tool. Likewise, the micro-invasive surgical instrument 10 can be dismantled without a tool into the components illustrated separately in FIG. 2. The broken line 19 that runs through the entire FIG. 2 indicates how these components are to be assembled.

The tool 20 is, in particular, durably connected with a transmission rod 40 that is provided to transmit a force and torque from the handling device 50 to the tool 20. The distal end of the transmission rod 40, which is not shown in FIG. 2, is coupled with the jaw members 25, 26 in such a way that a movement of the transmission rod 40 parallel to the longitudinal axis 29 of the tool 20 causes a synchronous movement of the jaw members 25, 26.

Bayonet coupling devices, not shown in FIG. 2, as well as a locking device coupled with the transmission rod 40 are provided on the proximal end 22 of the tool 20 and on the distal end 31 of the shaft 30. The jaw members 25, 26 are shown in FIG. 2 in firm outline in fully open positions 253, 263 and in dotted lines in the closed and open positions 251, 252, 261, 262 already described above with reference to FIG. 1. If the jaw members 25, 26 happen to be in the fully open positions 253, 263, the locking device that is coupled with the jaw members 25, 26 and the distal end of the transmission rod 40 and not shown in FIG. 2 is inactive. In this condition the transmission rod 40 can be inserted in a channel 34 foreseen for the transmission rod 40 in the shaft 30, and the proximal end 22 of the tool and the distal end 31 of the shaft can be detachably mechanically connected or coupled together by the bayonet coupling devices not shown in FIG. 2. In addition, in this unlocked condition a mechanical coupling of the proximal end 22 of the tool 20 and the distal end 31 of the shaft 30 can be released by the bayonet coupling devices that are not shown in FIG. 2.

If the jaw members 25, 26 are in the closed positions 251, 261, in the open positions 252, 262 or in positions situated in between, then the locking device that is coupled with the distal end of the transmission rod 40 and directly with the jaw members 25, 26 is situated in a working position or in a position inside a working range. In the working position or in the positions within the working range, the mechanical coupling of the proximal end 22 of the tool 20 is locked with the distal end 31 of the shaft 30 by the bayonet coupling devices not shown in FIG. 2. If the mechanical connection or coupling of the tool 20 and shaft 30 is locked, the tool 20 and shaft 30 cannot be separated from one another, or not necessarily without disturbance.

Instead of the bayonet coupling devices, the proximal end 22 of the tool 20 and the distal end 31 of the shaft 30 can comprise other coupling devices. In this case too, a locking device is provided on the tool 20 that locks the mechanical connection of the tool 20 and shaft 30 when the jaw members 25, 26 are found in the fully open positions 253, 263.

If the transmission rod 40 is inserted in the channel 34 of the shaft 30 and the proximal end 22 of the tool 20 is mechanically connected or coupled with the distal end 31 of the shaft 30, the proximal end 32 of the shaft 30 with the proximal end 42 of the transmission rod 40 that projects outward with respect to the proximal end 32 of the shaft 30 can be inserted in the handling device 50. For this purpose the handling device 50 comprises a recess 503 as indicated by a dotted line in FIG. 2.

To insert the proximal end 32 of the shaft 30 and the proximal end 42 of the transmission rod 40 in the handling device 50, the second gripping member 59 is first brought into a coupling position 593 as shown in unbroken lines in FIG. 2. If the second gripping member 59 is in the coupling position 593, then a rod coupling inside the handling device 50 but not shown in FIG. 2 is found in a coupling position in which it can receive or release the proximal end 42 of the transmission rod 40. If the proximal end 42 of the transmission rod 40 is inserted entirely in the handling device 50, the rod coupling that is inside the handling device 50 but is not shown in FIG. 2 is mechanically connected or coupled with the proximal end 42 of the transmission rod 40. In so doing, the second gripping member 59, depending on the positions of the jaw members 25, 26 (closed positions 251, 261, open positions 252, 262 or in between), moves into the first working position 591, the second working position 592 or a position between the first working position 591 and second working position 592.

If the proximal end 32 of the shaft 30 is inserted completely into the handling device 50, a bolt that is not shown in FIG. 2 grips in a surrounding groove 35 close to the proximal end 32 of the shaft 30, thus locking the proximal end 32 of the shaft 30 in a foreseen position in the handling device 50. Because of the locking of the proximal end 32 of the shaft 30 in the handling device 50, the mechanical coupling of the proximal end 42 of the transmission rod 40, with the rod coupling that is not shown in FIG. 2, is also indirectly locked in the interior of the handling device 50.

After the locking of the proximal end 32 of the shaft 30 in the handling device 50, and indirectly of the proximal end 42 of the transmission rod 40 in the handling device 50 in the rod coupling not shown in FIG. 2, the micro-invasive surgical instrument 10 is configured as shown in FIG. 1. By moving the second gripping member 59 in relation to the first gripping member 58 between the two working positions 591, 592, the jaw members 25, 26 can be moved between the closed positions 251, 261 and the open positions 252, 262. By rotating the rotary wheel 57 around the axis 578, the jaw members 25, 26 can be rotated around the longitudinal axis 29 of the tool 20.

Contrary to the depictions in FIGS. 1 and 2, the shaft 30 can comprise, close to its proximal end 32, a second rotary wheel that is positioned close to the distal end 51 of the handling device 50 if the proximal end 32 of the shaft 30 is inserted into the handling device 50. The shaft 30 can be rotated around the longitudinal axis of the proximal end 20 of the shaft 30 by means of this rotary wheel, which is not shown in FIGS. 1 and 2. This is particularly significant when the shaft 30 is curved, contrary to the depictions in FIGS. 1 and 2. In this case the curved shaft 30 and the tool 20 can be rotated independently of one another on the distal end 31 of the curved shaft 30.

Through pressure on the unlocking button 538, the bolt, not shown in FIG. 2, can be pushed against the force of a spring and can be disengaged from the groove 35 on the shaft 30. Then the proximal end 32 of the shaft 30 can be removed from the handling device 50. At the same time, the locking of the proximal end 42 of the transmission rod 40, on the rod coupling in the handling device 50 that is not shown in FIGS. 1 and 2, is also released.

Instead of one or—as shown in FIGS. 1 and 2—two movable jaw members 25, 26, the tool 20 can comprise a different active device, in particular a manipulator, for example a finger-shaped manipulator, or an electrode, for example a hook-shaped electrode.

Figure 3:
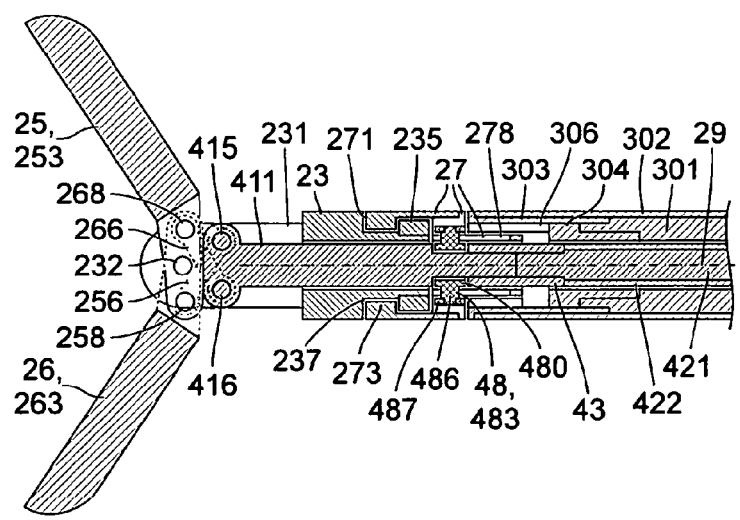
FIG. 3 shows a schematic depiction of a tool for a micro-invasive surgical instrument.
Figure 4:
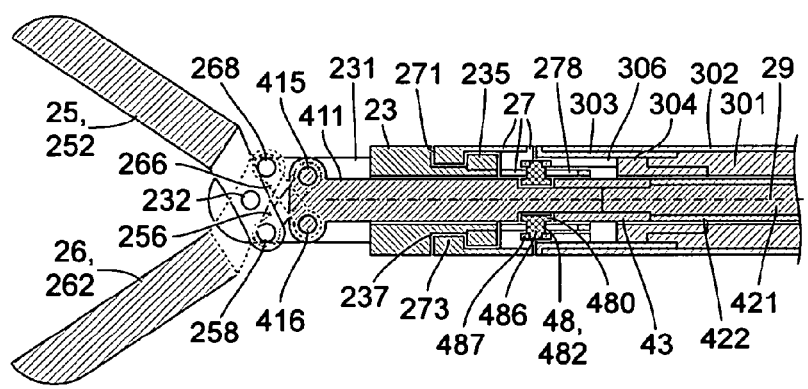
FIG. 4 shows another schematic depiction of the tool from FIG. 3.
Figure 5:
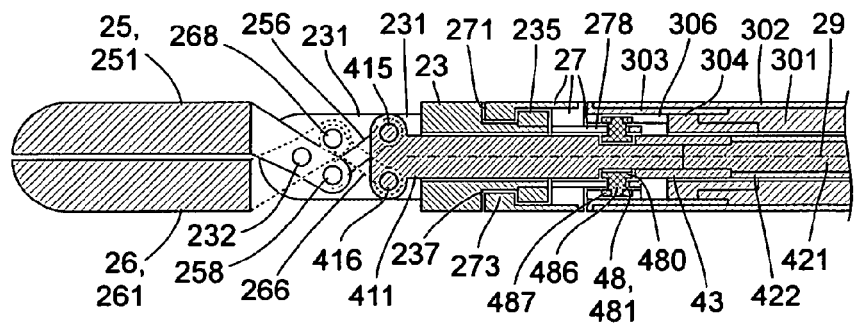
FIG. 5 shows another schematic depiction of the tool from FIGS. 3 and 4.

FIGS. 3 through 5 show schematic sectional views of an embodiment of the tool 20 presented above with reference to FIGS. 1 and 2. The sectional planes of FIGS. 3 through 5 are parallel to the planes of projection of FIGS. 1 and 2 and contain the longitudinal axis 29 of the tool 20 indicated in FIGS. 1 and 2. In addition to the tool 20, the distal end 31 of the shaft 30 is shown in each of FIGS. 3 through 5. In FIG. 3 the jaw members 25, 26 are shown in their fully open positions 253, 263, in which the mechanical connection between tool 20 and shaft 30 is unlocked; that is, it can be produced or released. In FIG. 4 the jaw members 25, 26 are shown in their open positions 252, 262, and the connection between tool 20 and shaft 30 is locked. In FIG. 5 the jaw members 25, 26 are shown in their closed positions 251, 261, and the connection between tool 20 and shaft 30 is likewise locked.

The tool comprises an articulated device 23, which is configured as fork-shaped with two blades in its distal area. One blade 231 is situated behind the sectional planes of FIGS. 3 through 5 and is recognizable in FIGS. 3 through 5. A second blade is configured and positioned symmetrically to the blade 231 shown in FIGS. 3 through 5 in relation to the sectional planes of FIGS. 3 through 5. The second blade is situated in front of the sectional plane of FIGS. 3 through 5 and therefore is not shown in FIGS. 3 through 5.

The tool 20 further includes a connecting component 27, which has an approximately sheath-shaped form with two essentially cylindrical-mantle-shaped portions with different diameters. The connecting component 27 can include two elements joined together, as indicated in FIGS. 3 through 5. The connecting component 27 comprises, close to its distal end 271, a collar 273 that protrudes radially inward and engages in a groove 237 on the articulated device 23. In the example illustrated in FIGS. 3 through 5, the groove 237 on the articulated device 23, for manufacturing reasons, is bounded by a ring 235, which is joined with the articulated device 23, after the connecting component 27 is positioned as foreseen.

The collar 273 on the connecting component 27 and the surrounding groove 237 on the articulated device 23 form a form-locked, low-play and low-friction permanent mechanical connection between the articulated device 23 and the connecting component 27. The mechanical connection between the connecting component 27 and the articulated device 23, formed by the collar 273 on the connecting component and the groove 237 on the articulated device 23, allows free rotation of the articulated device 23 in relation to the connecting component 27 around the longitudinal axis 29 of the tool 20. At the same time, the mechanical connection, formed by the collar 273 on the connecting component and the groove 237 on the articulated device 23, prevents relative axial sliding parallel to the longitudinal axis 29 of the tool 20 and any relative tipping movements around axes perpendicular to the longitudinal axis 29 of the tool 20.

In a proximal area the connecting component 27 is essentially tubular or cylindrical-mantle-shaped with a reduced diameter and slots 278 that are axial or extending parallel to the longitudinal axis 29 of the tool 20. The axial slots 278 form guides for a locking device 48, which is described in greater detail below. In addition, brackets are positioned on the proximal border of the connecting component 27 but are not shown in FIGS. 3 through 5 because they are situated outside the illustrated sectional plane. The shape and function of the brackets are described below with reference to FIGS. 6 through 9.

In FIGS. 3 through 5, in addition, the distal end of a shaft 30 can be recognized, mechanically connected or coupled with the tool 20. The shaft 30 includes a metallic tube 301 on whose distal end a bayonet sheath 304 and a supporting tube 303, surrounding the bayonet sheath 304 in a cylindrical-mantle shape, are joined together. The bayonet sheath 304 comprises L-shaped slots 306 extending from its distal border, each with a portion extending in axial direction and a portion extending in peripheral direction. The metallic tube 301 and the supporting tube 303 are surrounded, in mantle shape, by an isolating mantle 302 of an electrically insulating material.

The brackets, not shown in FIGS. 3 through 5, and the L-shaped slots 306 in the bayonet sheaths 304 on the distal end of the shaft 30 are positioned and configured to form corresponding bayonet coupling devices for detachable mechanical coupling or connection of the tool 20 and the shaft 30. The functioning of this bayonet coupling is described in greater detail below with reference to FIGS. 6 through 9.

The transmission rod 40, already indicated in FIG. 2, includes a distal portion 411 and a proximal portion 421, which are mechanically rigidly connected with one another by a connecting sheath 43.

On the extreme distal end, the distal portion 411 of the transmission rod 40 comprises two joints 415, 416. A first connection rod 256 links the first joint 415 on the distal end of the transmission rod 40 with a joint 258 on the first jaw member 25 that is at a distance from the axle 232. A second connection rod 266 links the second joint 416 on the distal end of the transmission rod 40 with a joint 268 on the second jaw member 26 that is at a distance from the axle 232. It can be recognized by comparing FIGS. 3 through 5 that a linear sliding of the transmission 40 parallel to the longitudinal axis 29 of the tool 20, by means of the connection rods 256, 266, causes a pivoting of the jaw members 25, 26 around the joints formed by the axle 232.

In a proximal area the distal portion 411 of the transmission rod 40 comprises a step-type reduced cross-section. At this location the distal portion 411 of the transmission rod 40, together with the connecting sheath 43, forms a ring-shaped surrounding groove in which a ring-type portion 480 of a locking device 48 is positioned. The ring-shaped portion 480 is guided, with low play and low friction, in the surrounding groove formed by the distal portion 411 of the transmission rod 40 and the connecting sheath 43. Because of the low-play, low-friction steering of the ring-shaped portion 480 on the transmission rod 40, the locking device 48 is rigidly connected with the transmission rod 40, aside from minor axial play, with respect to an axial movement parallel to the longitudinal axis 29 of the tool 20. At the same time, the locking device 48 can rotate in relation to the transmission rod 40 with low friction around the longitudinal axis 29 of the tool 20.

The locking device 48 comprises pins 486 that protrude radially outward and extend in each case through one of the axial slots 278 of the connecting component 27. Radially outside the axial slot 278, the locking device 48 in each case comprises a ring-shaped head 487 that is each joined onto the radial outer end of a pin 486. The radial pins 486 on the locking device 48 and the axial slots 278 on the connecting component 27 are configured and positioned in such a way that the locking device 48 can be slid with low friction inside a predetermined range, freely in relation to the connecting component 27, and at the same time is steered with low play through the slot 278 with respect to a rotation around the longitudinal axis 29 of the tool 20.

Axial sliding of the transmission rod 40 parallel to the axis 29 of the tool 20, as can be recognized in comparing FIGS. 3 through 5, thus leads to a corresponding sliding of the locking device 48. In particular, the locking device 48 is situated in the installation position 483 shown in FIG. 3 when the jaw members 25, 26 are in their fully open positions 253, 263 shown in FIG. 2. The locking device 48 is situated in the first working position 481 shown in FIG. 5 when the jaw members 25, 26 are in their closed positions 251, 261. The locking device 48 is situated in the second working position 486, shown in FIG. 4, when the jaw members 25, 26 are in their open positions 252, 262. In all positions 481, 482, 483 of the locking device 48, the transmission rod 40 and with it the articulated device 23 and jaw members 25, 26 be rotated in relation to the connecting component 27 and shaft 30 freely around the longitudinal axis 29 of the tool 20.

With the locking device 48 in the installation position 483 shown in FIG. 3, the locking device 48 does not engage in the L-shaped slot 306 in the bayonet sheath 304 on the distal end of the shaft 30. Therefore, with the locking device 48 in installation position 483, the connecting component 27 and the shaft 30 can be rotated in relation to one another in order to insert the bracket, which is not shown in FIGS. 3 through 5, in the L-shaped slot 306 in the bayonet sheath 304 and to remove it from it.

As mentioned, in FIG. 5 the locking device 48 is shown in a first working position 481 and the jaw members 25, 26 in their closed positions 251, 261. In FIG. 4 the locking device 48 is shown in its second working position and the jaw members 25, 26 in their open positions 252, 262. In both working positions 481, 482 the locking device 48 engages in axial portions of the L-shaped slot 306 in the bayonet sheath 304 on the distal end of the shaft 30. In particular, with the locking device 48 in both working positions 481, 482, the heads 487, positioned radially outside the axial slot 278 of the connecting component 27, engage in the axial portions of the L-shaped slot 306 in the bayonet sheath 304 on the distal end of the shaft 30. Consequently, the connecting component 27 and the shaft 30 cannot be rotated with respect to one another. The brackets on the proximal border of the connecting component 27, not shown in FIGS. 3 through 5, engage in the peripheral portions of the L-shaped 0slot 306 in the bayonet sheath 304 so that the connecting component 27 and thus the entire tool 20 are in a form-locked connection or coupling with the shaft 30. Instead of the heads 487, the locking device 48 can comprise one or more convex portions that are configured differently and engage in the axial portions of the L-shaped slot 306 in the bayonet sheath 304.

FIGS. 6 through 9 show schematic depictions of another embodiment of the tool 20 of the micro-invasive surgical instrument 10 from FIGS. 1 and 2.

Each of FIGS. 6 through 9 shows a section along a sectional plane B-B parallel to the longitudinal axis 29 of the tool 20 and a section along a sectional plane A-A perpendicular to the longitudinal axis 29 of the tool 20. The sectional plane B-B contains the longitudinal axis 29 of the tool 20 and corresponds to the sectional planes of FIGS. 3 through 5. The position of the sectional plane A-A is indicated in the depiction of the section along the plane B-B. The position of the sectional plane B-B is indicated in the depiction of the section along the plane A-A.

The tool 20 shown in FIGS. 6 through 9 is distinguished from the embodiment in FIGS. 3 through 5, in particular, by a different mechanical coupling between the transmission rod 40 and the jaw members 25, 26 to transmit a linear movement of the transmission rod 40 into pivoting movements of the jaw members 25, 26. The mechanical connection or coupling between the tool 20 and the distal end 31 of a shaft 30 resembles to a considerable degree the mechanical coupling in the embodiment presented above with reference to FIGS. 3 through 5. The mechanical connection between the tool 20 and the shaft 30, presented below with reference to FIGS. 6 through 9, and the locking of this connection correspond therefore to those for the embodiment in FIGS. 3 through 5.

The present mechanical coupling existing in the tool shown in FIGS. 6 through 9 between the transmission rod 40 and the jaw members 25, 26 stipulates, with the same pivot angles of the jaw members 25, 26, a linear sliding of the transmission rod 40 in a greater range. Accordingly, the axial slots 278 on the connecting component 27 in the tool 20 shown in FIGS. 6 through 9 are longer than in the embodiment in FIGS. 3 through 5.

Departing from a purely sectional depiction, the cuts along the planes B-B in FIGS. 6 through 9 each show in dotted lines the contour of the proximal end of the second jaw member 26 situated before the sectional plane or between the observer and the sectional plane. Further departing from a purely sectional depiction, in the depictions of the section along the planes A-A in FIGS. 6 and 7 the locking device 48 that is situated before the sectional plane or between the observer and the sectional plane is indicated in dotted lines in each case.

Because the first jaw member 25 is covered to a considerable degree in each of the depictions of the section along the plane B-B, departing from a purely sectional depiction in each case, the portion of the second jaw member 26 situated before the sectional plane is indicated in broken lines and the second blade 233 of the articulated device 23 situated before the sectional plane is indicated in dotted lines.

The proximal end of the second jaw member 26 comprises a pivot pin 265 that extends perpendicular to the sectional planes in FIGS. 6 through 9 and engages, with low play and low friction, in a corresponding groove or indentation, on the border of the blade situated before the illustrated sectional plane, that extends perpendicular to the longitudinal axis 29 of the tool 20. Thus the pivot pin 265 on the second jaw member 26, or the axis of symmetry of the pivot pin 265, defines the pivot axis 269 of the second jaw member 26.

The proximal area of the second jaw member 26, in addition, comprises a slot 267 that is at a distance from the pivot pin 265. The distal end of the transmission rod 40 is configured as a plate 46 with a control pin 466. The control pin 466 engages in the slot 267 on the second jaw member 26. In a comparison of FIGS. 6 and 7 on the one hand with FIGS. 8 and 9 on the other hand, it can be recognized that a linear movement of the transmission rod 40 between the distal position illustrated in FIGS. 6 and 7 and the proximal position illustrated in FIG. 9 causes a pivot motion of the second jaw member 26 because of the engagement of the control pin 466 in the driving slot 267.

The largely covered first jaw member in FIGS. 6 through 9 is symmetrical with the second jaw member 26 with respect to the longitudinal axis 29 of the tool 20. In other words, the first jaw member 25 goes through a 180-degree rotation around the longitudinal axis from the second jaw member and vice versa. This applies also to both blades 231, 233 of which the second blade 233 in FIGS. 6 through 9 is indicated in dotted lines.

In particular, the first jaw member 25 comprises a pivot pin that engages with little play and little friction in an indentation on the first blade 231. The pivot pin and indentation form a rotation axis 259 of the first component 25 that is indicated in FIGS. 6 through 9 and is perpendicular to the sectional plane of FIGS. 6 through 9. In addition, the proximal end of the first jaw member 25 comprises a slot and the plate 46 on the distal end of the transmission rod 40 a control pin 465, which is situated behind the illustrated sectional plane and engages in the slot on the proximal end of the first jaw member 25. The control pin 465 and the slot in the first jaw member 25 that does not appear in FIGS. 6 through 9 cause, in a linear movement of the transmission rod, a pivot motion of the first jaw member 25 symmetrically to the pivot motion of the second jaw member 26.

To guide the plate 46 on the distal end of the transmission rod 40, a guide pin 234 is provided that extends in the direction perpendicular to the sectional plane of FIGS. 6 through 9 between the two blades 231, 233 of the articulated device 23. The guide pin 234 engages in a straight guide slot 464 that extends in the axial direction in the plate 46 on the distal end of the transmission rod 40. In addition, the guide pin 234 engages in arched slots 254, 264 in the jaw members 25, 26. The engagement of the guide pin 234 in the arched guide slots 254, 264 on the jaw members 25, 26 ensures that the pivot pins 265 remain in the corresponding slots or indentations in the blades 231 of the articulated device 23.

Figure 6:
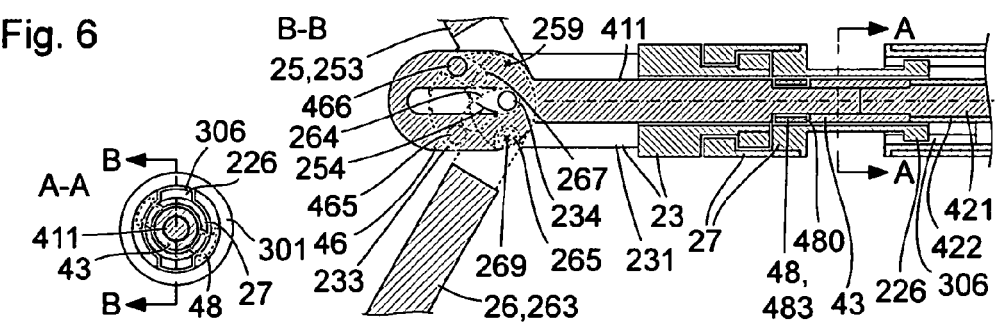
FIG. 6 shows a schematic depiction of another tool for a micro-invasive surgical instrument.
Figure 7:
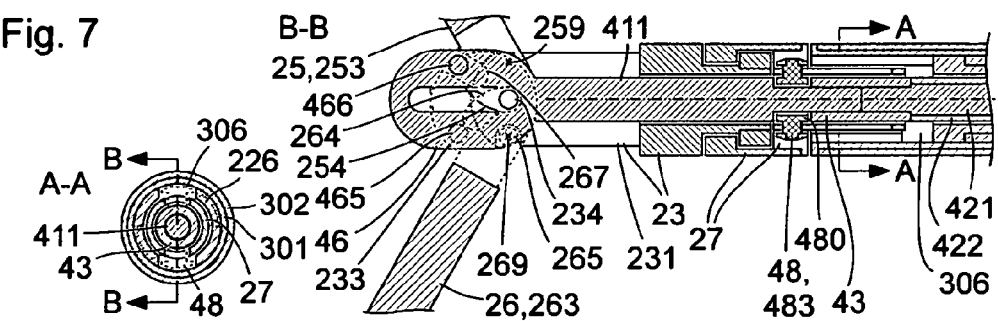
FIG. 7 shows another schematic depiction of the tool from FIG. 6.

In FIGS. 6 and 7 the jaw members 25, 26 are situated in their fully opened positions 253, 263 and the locking device 48 in its installation position 483. The connecting component 27 is shown in FIGS. 6 and 7 in various orientations with respect to the rotation around the longitudinal axis 29 of the tool 20. In the orientation of the connecting component 27 shown in FIG. 6, the axial slots 278, the pins 486 and the heads 487 are situated outside the sectional plane B-B, and the brackets 226 on the proximal border of the connecting component 27 are in the sectional plane B-B. In this orientation of the connecting component 27 in relation to the distal end 31 of the shaft 30, the brackets 226, as indicated in FIG. 6, can be inserted in the portions of the L-shaped slots 306 that extend in axial direction. The brackets 226 on the proximal border of the connecting component 27 of the tool 20 and the L-shaped slots 306 on the distal end of the shaft 30 thus constitute coupling devices or components of coupling devices for detachable mechanical coupling of the connecting component 27 with the distal end 31 of the shaft 30.

If the brackets 226 are inserted completely in the portions of the L-shaped slots 306 in the bayonet sheath 304 that extend in axial direction, the connecting component 27 can be rotated with respect to the shaft 30 in clockwise direction (based on the depictions of the sections along the planes A-A in FIGS. 6 through 9). In so doing, the brackets 226 are slid in the portions of the L-shaped slots 306 in the bayonet sheath 304 that extend in peripheral direction. After the rotation of the connecting component 27 with respect to the shaft 30, a form-locked connection is established, based on axial tractive forces, between the tool 20 and the shaft 30.

As long as the locking device 48 is situated in the installation position shown in FIGS. 6 and 7, the form-locked connection between the tool 20 and shaft 30 can nevertheless be released again through a contrary rotation or turning of the connecting component 27 (in counterclockwise direction) with respect to the shaft 30.

Figure 8:
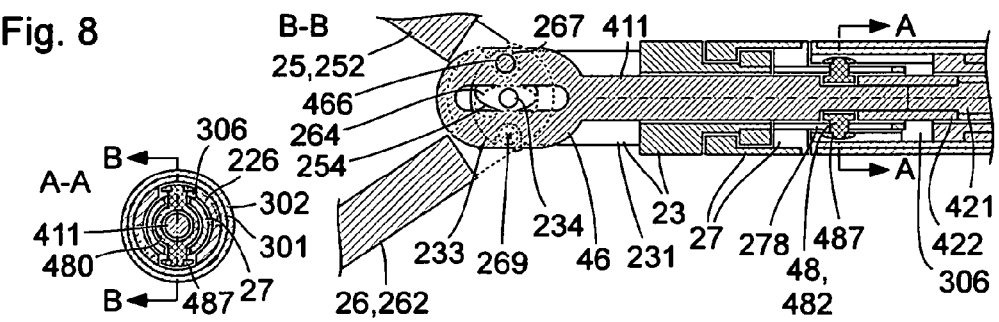
FIG. 8 shows another schematic depiction of the tool from FIGS. 6 and 7.
Figure 9:
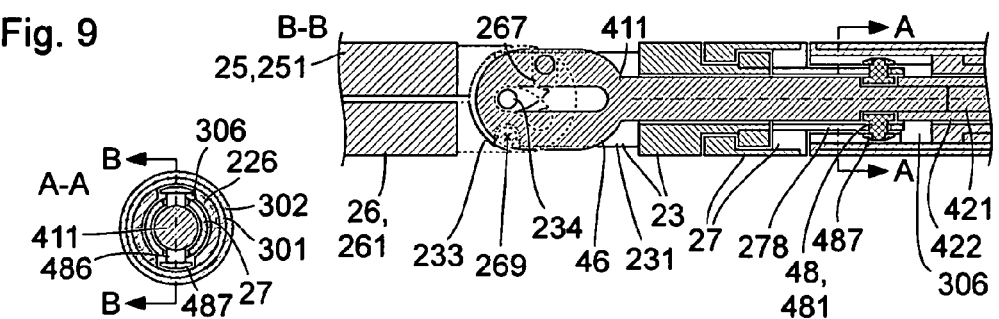
FIG. 9 shows another schematic depiction of the tool from FIGS. 6 through 8.

If the locking device 48 is situated in the working positions 482, 481 shown in FIGS. 8 and 9, the radially outward situated ends of the pins 486 and the heads 487 positioned on the radially outward situated ends of the pins 486 engage in the axial portions of the L-shaped slots 306 in the bayonet sheath 304. The connecting component 27 cannot be rotated with respect to the shaft 30, and the mechanical connection or coupling between the tool 20 and the shaft 30 is locked.

Figure 10:
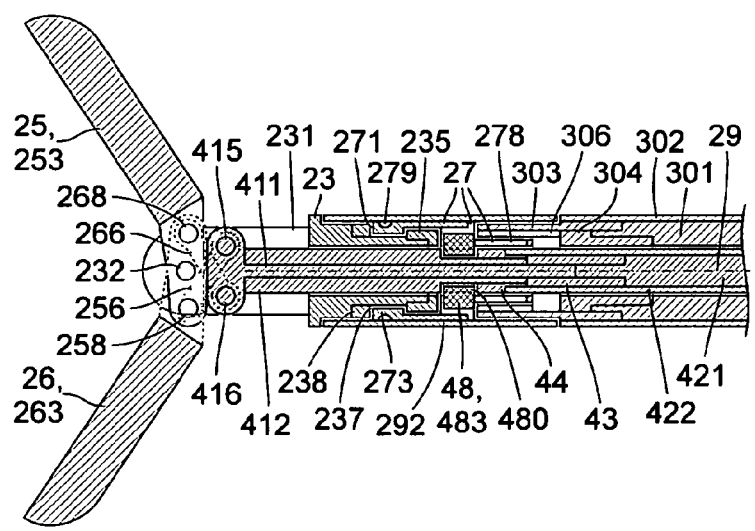
FIG. 10 shows a schematic depiction of another tool for a micro-invasive surgical instrument.
Figure 11:
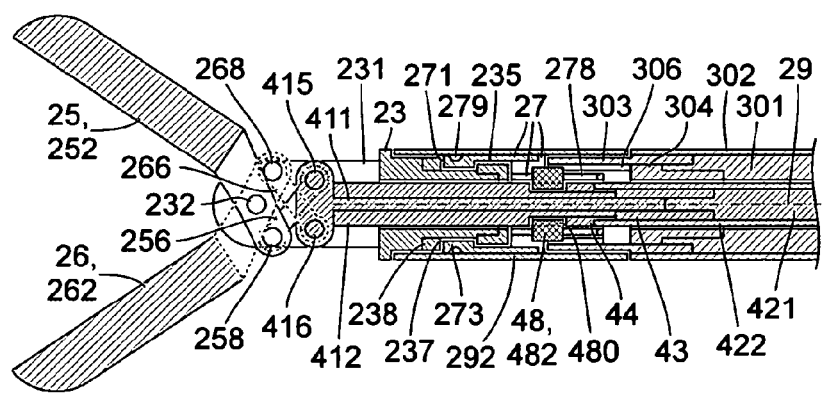
FIG. 11 shows another schematic depiction of the tool from FIG. 10.
Figure 12:
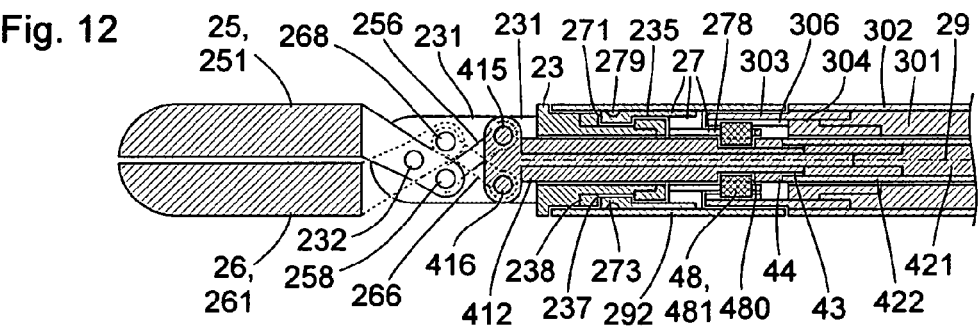
FIG. 12 shows another schematic depiction of the tool from FIGS. 10 and 11.

FIGS. 10 through 12 show schematic sectional depictions of an additional embodiment of the tool 20 described above with reference to FIGS. 1 and 2. The sectional planes of FIGS. 10 through 12 are parallel to the planes of projection of FIGS. 1 and 2, correspond to the sectional planes of FIGS. 3 through 5 and the sectional planes B-B of FIGS. 6 through 9, and contain the longitudinal axis 29 of the tool 20 indicated in FIGS. 1 and 2. In each of FIGS. 10 through 12, the distal end 31 of the shaft 30 is shown, in addition to the tool 20. In FIG. 10 the jaw members 25, 26 are depicted in their fully open positions 253, 263 in which the mechanical connection between the tool 20 and the shaft 30 is unlocked, that is, can be produced or released. In FIG. 11 the jaw members 25, 26 are shown in their open positions 252, 262, and the connection between the tool 20 and shaft 30 is locked. In FIG. 12, with the jaw members 25, 26 shown in their closed positions 251, 261, the connection between the tool 20 and shaft 30 is likewise locked.

The embodiment in FIGS. 10 through 12 resembles in some respects the embodiment in FIGS. 3 through 5 and to a lesser extent also the embodiment in FIGS. 6 through 9. Characteristics of the embodiment in FIGS. 10 through 12, which resemble characteristics of the embodiments in FIGS. 3 through 5, are not described again. As described below, the embodiment in FIGS. 10 through 12 is distinguished from the embodiment in FIGS. 3 through 5 primarily by the transmission rod 40, by the locking device 48 and by the mechanical connection of the proximal area of the articulated device 23 with the connecting component 27.

The articulated device 23 in its proximal area has a cross-section with circular or essentially circular contour that becomes smaller in several stages from the distal to the proximal direction. A circular-shaped contact component 238 is positioned bordering on a front surface of the articulated device 23 that is circular-shaped, flat and oriented toward the proximal end and that is configured by one of these stages. The compact component 238 contains a metal or other electrically conductive material that, in particular, can be welded or soldered.

A ring 235 is mechanically rigidly connected with the proximal end of the articulated device 23. For example, the articulated device 23 at its proximal end comprises an external thread and the ring 235 comprises a corresponding internal thread. Alternatively or in addition, the ring 235 can be connected with the articulated device 23 by cementing, soldering or welding.

Between the contact component 238 and the ring 235, the articulated device 23 comprises a ring-shape groove 237 whose circular flanks are configured by the proximal front side of the contact component 238 and the distal front side of the ring 235. A radially inward-projecting collar 273 of a connecting component 27 that largely resembles the connecting component of the embodiment in FIGS. 3 through 5 engages in this groove 237. For installation, the collar 273 of the connecting component 27 is first conducted to the contact component 238, and then the ring 235 is affixed to the articulated device 23.

The collar 273 and groove 237 have surfaces that correspond to one another. By the engagement of the collar 273 in the groove 237, the connecting component 27 is held in form-locked connection on the articulated device 23 with low play and low friction. The connecting component 27 can rotate with respect to the articulated device 23 only around the longitudinal axis 29 of the tool 20; however—barring desired or unavoidable play—it can neither move parallel to the longitudinal axis 29 nor be tipped around axes perpendicular to the longitudinal axis 29.

The tool 20 in the area of the connecting component 27 comprises an essentially cylindrical-mantle-shaped insulation sleeve 292, which protrudes distally and especially also proximally with respect to the connecting component 27 in the direction parallel to the longitudinal axis 29 of the tool 20. In particular, the distal border of the insulation sleeve 292 is positioned distally from the contact component 238.

The inner surface of the insulation sleeve 292, at least in a part of the area in which it is contiguous with the outer surface of the connecting component 27, is joined by cement or other means in a firmly bonded and/or form-locked and/or force-locked connection. In particular, the outer surface of the connecting component 27 comprises a longitudinal corrugation or other structuring that supports transmission of torque from the insulation sleeve 292 to the connecting component 27.

The connecting component 27, in the area of the collar 273, comprises on its outer surface a ring-shaped groove 279, which in the example illustrated here has a semicircular cross-section. The groove 279 is especially configured to receive superfluous cement upon sliding the insulation sleeve 292 onto the connecting component 27 parallel to the longitudinal axis 29 of the tool 20 from proximal to distal. In particular, the edge on the distal border of the groove 279 acts as a wiping edge for cement that is left on the inside of the insulation sleeve 292. This measure can prevent this excess cement on the distal side of the connecting component 27 from forming an undesired firm bonding of the insulation sleeve 292 with the contact component 238 or with the articulated device 23.

The transmission rod 40 is distinguished from the transmission rod of the embodiment in FIGS. 3 through 5, in particular, by an insulation sleeve 412. The insulation sleeve 412 extends approximately over the entire length of the distal portion 411 of the transmission rod 40 and surrounds the distal portion 411 of the transmission rod 40 in a mantle shape, in particular in an essentially cylindrical-mantle shape. The outer contour of the cross-section of the insulation sleeve 412 is circular, whereby the radius at one point changes in stages. A ring 44 is positioned close to the proximal end of the insulation sleeve 412. The ring 44 includes in particular an electrically insulating material and surrounds the insulation sleeve 412. The ring 44 is, in particular, firmly bonded and/or force locked and/or friction locked with the insulation sleeve 412.

An insulation mantle 422 encloses the proximal portion 421 of the transmission rod 40 in a mantle shape, in particular in cylindrical-mantle shape. Close to its distal end the insulation mantle 422 overlaps partly with the ring 44. The insulation sleeve 412, ring 44 and insulation mantle 422 thus form a complete electrical insulation of the transmission rod in the area in which the transmission rod 40 is positioned inside the tool 20 and/or inside the shaft 30. The transmission rod 40 is not electrically insulated only in the area of the joints 415, 416 on the distal end of the transmission rod 40. The conductivity of the materials of the distal portion 411 and of the proximal portion 421 of the transmission rod 40, as well as the connecting sheath 43, makes it possible to conduct an electrical potential to the distal end of the transmission rod 40.

A locking device 48 includes a ring-shaped portion 480. The ring-shaped portion 480 of the locking device 48 is positioned in a surrounding groove on the transmission rod 40 between the step-shaped cross-section modification of the insulation sleeve 412 and the ring 44. The distal annular-shaped front surface of the ring-shaped portion 480 is contiguous with an annular surface that is oriented proximally and that is configured by the step-shaped cross-section modification of the insulation sleeve 412. The proximal annular-shaped front surface of the ring-shaped portion 480 is contiguous with an annular-shaped front surface of the ring 44 that is oriented distally. The ring-shaped portion 480 of the locking device 48 is thereby guided in the surrounding groove with low play and low friction. Thus the locking device 48 can be rotated with respect to the transmission rod 40 around the longitudinal axis 29 of the tool 20, but cannot be slid in the direction parallel to the longitudinal axis 29 of the tool 20.

The locking device 48 is distinguished from the locking devices of the embodiments in FIGS. 3 through 5 and 6 through 9, in particular, by a one-piece structure. Instead of annular heads that are joined on the radially outer ends of pins, the locking device 48 of the embodiment in FIGS. 10 through 12 comprises T-shaped heads that are produced in a single piece with the annular portion 480 of the locking device 48. Two heads are situated in the sectional plane of FIGS. 10 through 12. As is described below with reference to FIGS. 13 through 16, each head comprises a T-shaped cross-section in a sectional plane perpendicular to the longitudinal axis 29 of the tool 20.

Described below, with reference to FIGS. 13 through 16, is a locking effect of the locking device 48 on a mechanical connection or coupling of the tool 20 with the distal end 31 of a shaft 30 (see also FIGS. 3 through 5, 6 through 9 and 10 through 12). The mechanical connection or coupling between the tool 20 and the shaft 30 occurs by means of the L-shaped slot 306 in the distal area of the bayonet sheath 304 on the distal end of the shaft 30 and of the bracket 226 on the proximal end of the connecting component 27 of the tool 20. FIGS. 13 through 16 therefore show only the connecting component 27, the distal end of the shaft 30 with the bayonet sheath 304 and the transmission rod 40 with the locking device 48.

Each of FIGS. 13 through 16 shows, at the left, a section along a plane A-A perpendicular to the longitudinal axis 29 of the tool 20 (see also FIGS. 3 through 5, 6 through 9 and 10 through 12) and, at the right, two overhead views of the connecting component 27, of the distal end of the shaft 30 with the bayonet sheath 304 and of the transmission rod 40. The sectional planes A-A of FIGS. 13 through 16 are distinguished partly by a slight parallel displacement. The planes of projection of the depictions to the right in FIGS. 13 through 16 are each perpendicular to the sectional plane A-A, parallel to the longitudinal axis 29 of the tool 20 (see also FIGS. 3 through 5, 6 through 9 and 10 through 12) and perpendicular to the section planes and planes of projection of FIGS. 3 through 12. To the right in FIGS. 13 through 16, the position of the sectional plane A-A is indicated in each case.

The overhead views of the connecting component 27, distal end of the shaft 30 and transmission rod 40 are each shown twice above one another to the right in FIGS. 13 through 16. In the upper view in each case, the contours of the bayonet sheath 304 are shown in continuous lines at the distal end of the shaft 30, while the transmission rod 40, to the extent that it runs inside the connecting component 27 or the shaft 30, is indicated only in broken lines. In the lower view in each case, the transmission rod 40—to the extent that it is not positioned inside the connecting component 27—is shown in continuous lines and the shaft 30 with the bayonet sheath 304 is indicated merely in non-contoured hatching.

To the right in FIGS. 13 through 16, the L-shaped form of each slot 306 in the distal area of the bayonet sheath 304 can be recognized. The bayonet sheath 304 includes in particular two L-shaped slots 306, which are displaced by 180 degrees with respect to one another, based on the longitudinal axis 29 of the tool 20 (see also FIGS. 3 through 5, 6 through 9 and 10 through 12). Each L-shaped slot in the bayonet sheath 304 includes an axial portion and a peripheral portion. The axial portion extends in the axial direction, and the peripheral portion extends in the peripheral direction.

In FIGS. 13 through 16, in addition, the aforementioned axial slot 278, while difficult to perceive in FIGS. 3 through 5, 6 through 9 and 10 through 12, is recognizable on the connecting component 27 that extends in the axial direction. It can be recognized each time in the sections along the planes A-A that each head 487 has a T-shaped cross-section and extends in the radial direction through one of the axial slots 278.

Figure 13:
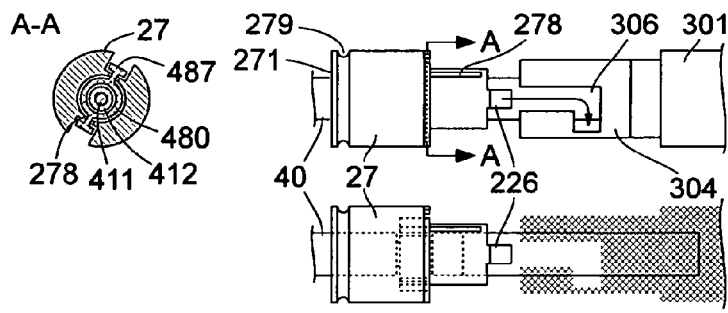
FIG. 13 shows a schematic depiction of coupling devices.
Figure 14:
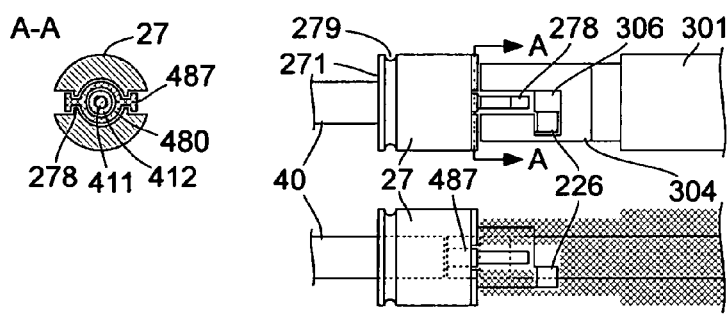
FIG. 14 shows another schematic depiction of the coupling devices from FIG. 13.

In the situations depicted in FIGS. 13 and 14 the locking device 48 is situated in the installation position 483 that is also shown in FIGS. 3, 6 and 10. The bolt 484 is largely concealed inside the connecting component 27. The bracket 226, as indicated by an arrow in FIG. 13, can be inserted into the peripheral portion of the L-shaped slot 306 in the bayonet sheath through the axial portion of the L-shaped slot 306 by an axial movement and a subsequent rotary movement of the connecting component 27 in relation to the shaft 30.

Figure 15:
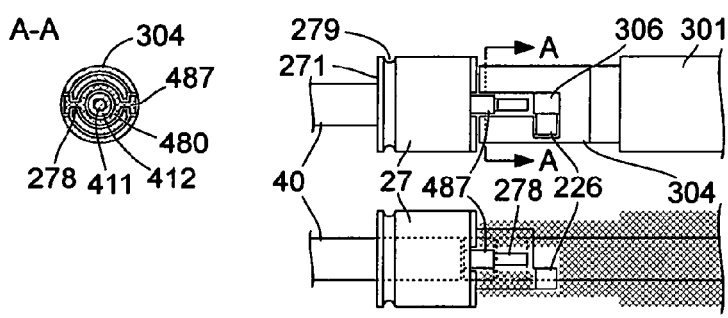
FIG. 15 shows another schematic depiction of the coupling devices from FIGS. 13 and 14.
Figure 16:
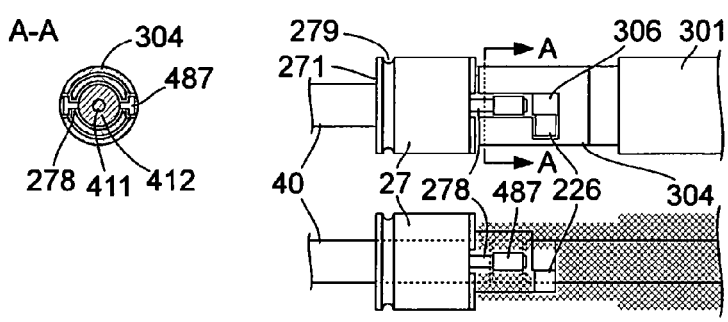
FIG. 16 shows another schematic depiction of the coupling devices from FIGS. 13 through 15.

In the situations depicted in FIGS. 14, 15 and 16, the bracket 226 is found in the peripheral portion of the L-shaped slot 306 in the bayonet sheath 304 on the distal end of the shaft 30. If the bracket 226 is situated in the peripheral portion of the L-shaped slot 306, a mechanical connection is formed between the connecting component 27 and the bayonet sheath 304 or the distal end of the shaft 30 by form-locking between the bracket 226 and the peripheral portion of the L-shaped slot 306 with respect to tractive forces. A form-locking connection, which absorbs tractive forces, is also thereby formed between the entire tool 20 and the shaft 30. Thus the brackets 226 on the proximal end of the connecting component 27 of the tool 20 and the L-shaped slots 306 in the bayonet sheath 304 on the distal end of the shaft 30 form coupling devices or are components of coupling devices for detachable mechanical coupling of the connecting component 27 with the distal end of the shaft 30.

As long as the locking device 48, as shown in FIGS. 13 and 14, is in the installation position 483 as also shown in FIGS. 3, 6 and 10, the bracket 226 can be removed again from the L-shaped slot 306 in the bayonet sheath 304 on the distal end of the shaft 30 by a rotary movement followed by an axial movement of the connecting component 27 in relation to the shaft 30.

In the situation shown in FIG. 15, the locking device 48 is in the second working position 482 also shown in FIGS. 4, 8 and 11. In the situation shown in FIG. 16, the locking device 48 is in the first working position 481 also shown in FIGS. 6, 9 and 12. In all positions 481, 482, 483, each of the T-shaped heads 487 of the locking device 48 grips in radial direction through a slot 278 on the proximal end of the connecting component 27. With the locking device both in the first working position 481 and in the second working position 482, each of the T-shaped heads 487 of the locking device 48 thrusts, in addition, into the axial portion of an L-shaped slot 306 in the bayonet sheath. Thus the locking device 48 and in particular its T-shaped heads 487, in the working positions 481, 482, block relative rotation of the connecting component 27 and bayonet sheath 304. Thus the locking device 48 holds or blocks the bracket 226 in the peripheral portion of the L-shaped slot 306 in the bayonet sheath 304. The locking unit 48, in the working positions 481, 482 shown in FIGS. 4, 5, 8, 9, 11 and 12, thereby locks the mechanical connection or coupling of the tool 20 with the distal end of the shaft 30.

The structure of the tool 20 as shown in FIGS. 10 through 12 is suited for a bipolar micro-invasive surgical instrument with which a high-frequency alternative current is applied between the jaw members 25, 26 in order to atrophy tissue gripped or severed by the jaw members 25, 26 with a flow of current, in particular to coagulate protein. The contacting of the jaw members 25, 26 or the application of electric current and electric power to the jaw members 25, 26 is described below with reference to FIGS. 17 and 18.

Figure 17:
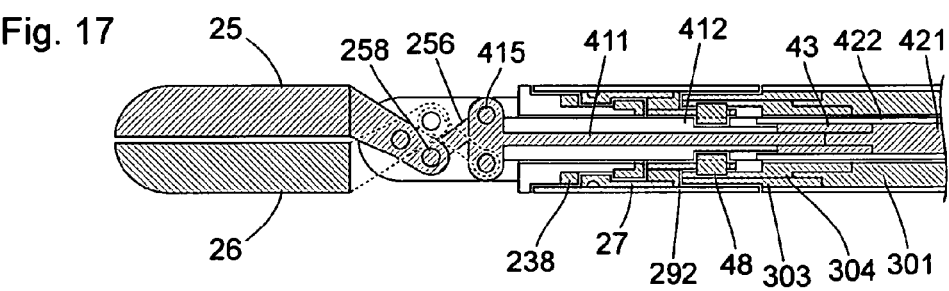
FIG. 17 shows another schematic depiction of the tool from FIGS. 10 through 12.
Figure 18:
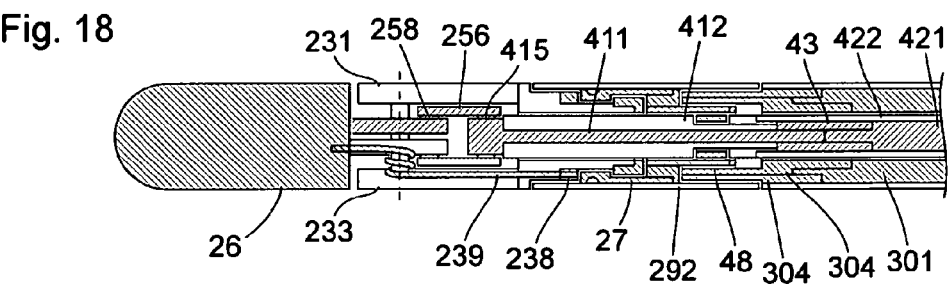
FIG. 18 shows another schematic depiction of the tool from FIGS. 10 through 12 and 17.

The tool 20 is shown in FIGS. 17 and 18 with the distal end 31 of the shaft 30 in schematic sectional depictions. The sectional plane of FIG. 17 corresponds to the sectional planes of FIGS. 3 through 12. The sectional plane of FIG. 18 is perpendicular to the sectional planes of FIGS. 3 through 12 and 17, parallel to the planes of projection of the depictions at the right in FIGS. 13 through 16, and parallel to the longitudinal axis 29 of the tool 20.

In FIGS. 17 and 18, all the electrically conductive elements, which are electrically conductively connected with the first jaw member 25, are shown with hatch lines that run from below left to above right. All elements that are electrically conductively connected with the second jaw member 26 are shaded with hatch lines running from below right to above left. Elements that comprise electrically insulating materials are, like hollow spaces, not hatched and are only partly labeled with reference numbers. To depict the electrically conductive connection to the jaw members, FIGS. 17 and 18 differ from a sectional depiction in the area to the left of the center of the drawing or distal from the joints 415, 416 on the distal end of the transmission rod 40. In this distal area, FIG. 18 corresponds instead to an overhead view.

The first jaw member 25 is electrically contacted by the proximal portion 421 of the transmission rod 40, the connecting sheath 43, the distal portion 411 of the transmission rod 40, the joint 415, the first connection rod 256 and the joint 258 on the first jaw member 25. The second jaw member 26 is contacted by the metal tube 301 of the shaft 30, the bayonet sheath 304, the bracket 226 that is situated in neither of the two sectional planes of FIGS. 10 and 11 (see also FIGS. 6 and 13 through 16), the locking device 48, the connecting component 27, the contact component 238 and an elastic electrically conductive component 239 that is shown only in FIG. 18.

The elastic electrically conductive component 239 is formed in particular by a metallic wire that comprises a helical portion on the axle 232. The proximal end of the elastic electrically conductive component 239 is connected with the contact component 238, for example plugged in, clamped, welded or soldered. In particular, the proximal end of the elastic electrically conductive component 239, contrary to the depiction in FIG. 11, is plugged into the lumen of a tube that is soldered or welded together with the contact component 238 and optionally soldered or welded with the tube. A slight curvature of the proximal end of the elastic electrically conductive component 239 can cause an elastic clamping of the proximal end of the elastic electrically conductive component 239 in the tube and thus a reliable contact if the elastic electrically conductive component 239 is not soldered or welded with the tube or the contact component 238. The distal end of the elastic electrically conductive component 239 is electrically conductively connected with the second jaw member 26, for example clamped, plugged in, soldered or welded.

The proximal portion of the elastic electrically conductive component 239 is, in particular, positioned in one of the blades 231, 233 of the articulated device 23. A distal portion of the elastic electrically conductive component 239 is positioned in particular in an electrically insulating portion of the second jaw member, which includes the bearing on the axle 232 and the joint 268 to the second connection rod 266.

The circular-shaped proximal front surface of the contact component 238 is contiguous with the circular-shaped distal front surface of the connecting component 27. The mechanical contact of the two front surfaces simultaneously forms an electrically conductive contact. The proximal front surface of the contact component 238 and the distal front surface of the connecting component 27 are thus corresponding contact surfaces. The mechanical and electrical contact exists independently of the rotational position of the tool 20 with respect to the connecting component 27 and to the bayonet sheath 304 that is mechanically and electrically coupled with the connecting component 27.

If the jaw members 25, 26 are moved proximally in the direction toward the closed positions 251, 261 by a tractive force acting on the transmission rod 40, the proximal front surface of the contact component 238 and the distal front surface of the connecting component 27 are pressed together. Therefore the mechanical and electrical contact between the contact component 238 and the connecting component 27 exists even in the case of a mechanical play of the collar 273 in the groove 237, at least when the jaw members 25, 26 are closed against a mechanical resistance.

In the embodiments presented above, the transmission rod 40 is configured both to transmit a translational movement in a direction parallel to the shaft 30 or to its longitudinal axis and a corresponding pulling and/or pushing force, and to transmit a rotational movement and a corresponding torque to the tool 20. Contrary to the explanation with reference to the drawings, the tool 20 on the distal end 31 of the shaft 30 can be rotatable merely around the longitudinal axis of the distal end 31 of the shaft 30 or around another axis. For example, the tool 20 includes a finger-shaped or other manipulator or an electrode in hook or loop form or in another shape. In this case, a configuration of the transmission rod 40 to transmit a translational movement in a direction parallel to the shaft 30 and to transmit a corresponding force is required only to the extent that it is necessary for moving the locking device 48.

Figure 19:
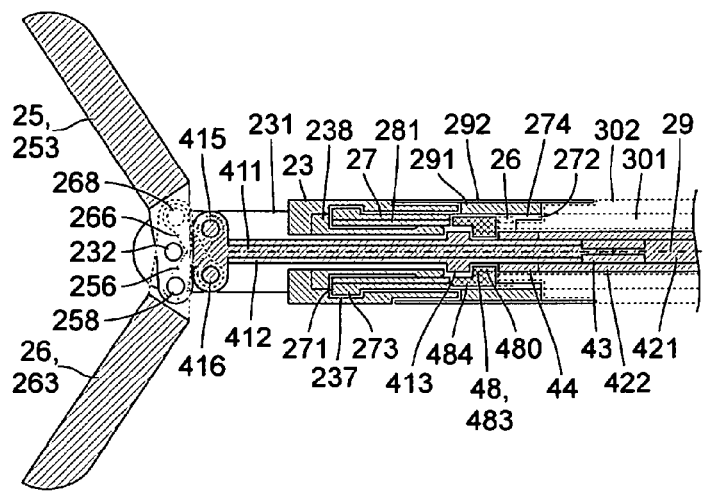
FIG. 19 shows a schematic depiction of another tool for a micro-invasive surgical instrument.
Figure 20:
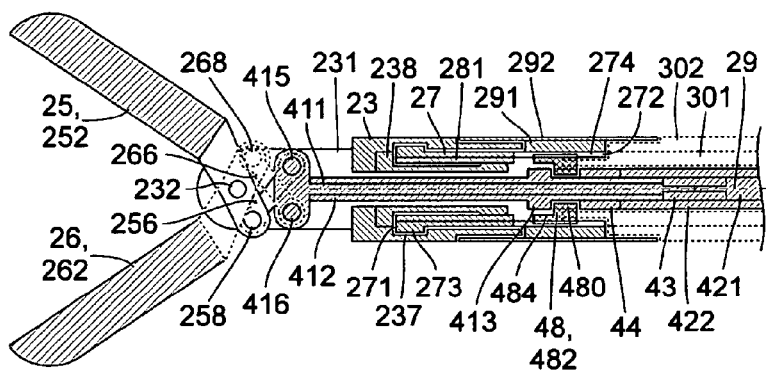
FIG. 20 shows another schematic depiction of the tool from FIG. 19.
Figure 21:
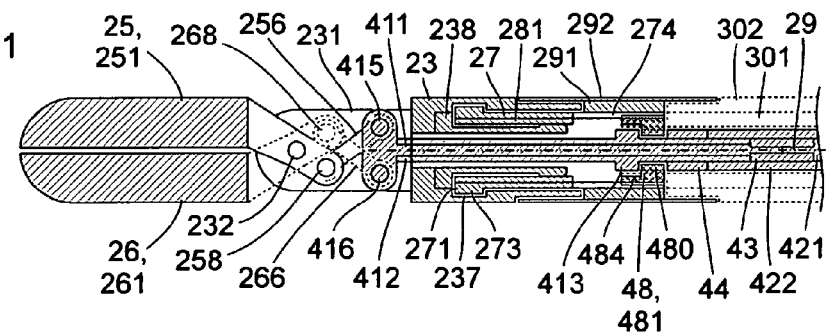
FIG. 21 shows another schematic depiction of the tool from FIGS. 19 and 20.

FIGS. 19 through 21 show schematic sectional depictions of another embodiment of the tool 20 presented above with reference to FIGS. 1 and 2. The sectional planes of FIGS. 19 through 21 are parallel to the planes of projection of FIGS. 1 and 2, correspond to, among other things, the sectional planes of FIGS. 3 through 5 and 10 through 12, and contain the longitudinal axis 29 of the tool 20 indicated in FIGS. 1 and 2. In addition to the tool 20, in each of FIGS. 19 through 21 the distal end 31 of the shaft 30 is shown in hatched lines. In FIG. 19 the jaw members 25, 26 are shown in their fully open positions 253, 263, in which the mechanical connection between the tool 20 and the shaft 30 is unlocked; that is, it can be produced and released. In FIG. 20 the jaw members 25, 26 are shown in their open positions 252, 262, and the connection between the tool 20 and shaft 30 is locked. In FIG. 21 the jaw members 25, 26 are shown in their closed positions 251, 261, and the connection between the tool 20 and shaft 30 is likewise locked.

The tool comprises an articulated device 23, which is configured in a distal area as fork-shaped with two blades. One blade 231 is situated behind the sectional planes of FIGS. 19 through 21 and can be recognized in FIGS. 19 through 21. A second blade is configured and positioned symmetrically to the blade 231 shown in FIGS. 19 and 21 with respect to the sectional planes of FIGS. 19 through 21. The second blade is situated before the sectional plane of FIGS. 19 through 21 and is therefore not shown in FIGS. 19 through 21.

Between the two blades, an axle 232 is positioned whose axis is perpendicular to the sectional planes and planes of projection of FIGS. 19 through 21. The ends of the axle 232 are each affixed in one of the blades 231. The jaw members 25, 26 are each mounted on the axle 232 so that they can rotate around a pivot axis perpendicular to the sectional planes and planes of projection of FIGS. 19 through 21.

In a proximal area the articulated device 23 is rotation-symmetrical or essentially rotation-symmetrical to the longitudinal axis 29 of the tool 20 and essentially sheath-shaped. In this area the articulated device 23 comprises a surrounding or ring-shaped groove 237, which opens inward or extends out from the inside of the articulated device 23 that is sheath-shaped there.

The tool 20 further includes a connecting component 27. The connecting component 27 comprises a sheath-shaped or tubular or cylindrical-mantle-shaped basic form, which is essentially rotation-symmetrical to the longitudinal axis 29 of the tool 20. The connecting component comprises a few departures from rotation symmetry, which are explained below with reference to FIGS. 19 through 25.

The connecting component 27 comprises close to its distal border 271 a collar 273 that engages in the surrounding groove 237 on the articulated device 23. The collar 273 on the connecting component 27 and the surrounding groove 237 on the articulated device 23 form a form-locked and low-play permanent mechanical connection between the articulated device 23 and the connecting component 27. The mechanical connection between the connecting component 27 and articulated device 23, formed by the collar 273 on the connecting component and the groove 237 on the articulated device 23, allows free rotation of the articulated device 23 in relation to the connecting component 27 around the longitudinal axis 29 of the tool 20. Simultaneously the mechanical connection formed by the collar 273 on the connecting component and the groove 237 on the articulated device 23 resists relative axial sliding parallel to the longitudinal axis 29 of the tool 20 and relative tipping movements around axes perpendicular to the longitudinal axis 29 of the tool 20.

The connecting component 27 further comprises radial slots extending from its distal end 271 that are not recognizable in FIGS. 19 through 21 and are described below with reference to FIGS. 22 through 25. In addition, the connecting component 27 comprises T-shaped slots 274 extending from its proximal end 272 that are partly recognizable in FIGS. 19 through 21.

The outer surface of a supporting sheath 281 is contiguous with the inner surface of the connecting component 27 that is essentially cylindrical-mantle-shaped, apart from the aforementioned axial slots. The supporting sheath 281 is essentially tubular in shape and comprises, in particular, a smaller length than the connecting component 27.

In the area of the distal end of the sheath-shaped portion of the articulated device 23, a contact component 238 is in a form-locked, firmly bonded or force-locked connection with the articulated device 23 that extends radially inside the supporting sheath in sheath shape in the proximal direction and, close to its proximal end, is contiguous with a contact surface on the inside of the supporting sheath 281.

An essentially cylindrical-mantle-shaped handling ring 291 encloses a proximal area of the connecting component 27 and is, in particular, in a firmly bonded and/or force-locked and/or form-locked connection with it. An essentially cylindrical-mantle-shaped insulation sleeve 292 encloses the handling ring 291 and stands opposite to it in both axial directions. The insulation sleeve 292 is in a firmly bonded and/or force-locked and/or form-locked connection with the handling ring 291.

The connecting component 27, supporting sheath 281, handling ring 291 and insulation sleeve 292 thus form a rigid mechanical unit, which can be grasped by medical staff on the outer surface of the insulation sleeve 292 and can be rotated with respect to the articulated device 23. The outer surface of the insulation sleeve is particularly intended for handling by medical staff during the mechanical coupling of the tool 20 with a distal end 31 of a shaft 30.

The distal end of a shaft 30 (compare FIGS. 1 and 2) indicated in dotted lines in FIGS. 19 through 21 includes a metallic tube 301 or other unbendable tube of a non-metallic material that is enclosed by an insulating mantle 302. Several brackets 36 are positioned close to the distal border of the metallic tube 301. The brackets 36 are configured with respect to their arrangement and shape in such a way that they can connect in the manner of a bayonet coupling to the T-shaped slots 274 on the connecting component 27 that are only partly recognizable in FIGS. 19 through 21, in order to form a detachable mechanical connection between the distal end of the shaft 30 and the connecting component 27. The T-shaped slots 274 on the connecting component 27 and the brackets 36 on the distal border of the metallic tube 301 thus form coupling devices or are components of coupling devices to detachably mechanically couple the connecting component 27 with the distal end 31 of the shaft 30.

The transmission rod 40 already sketched in FIG. 2 includes a distal portion 411 in the distal area depicted in FIGS. 19 through 21. The distal portion 411 of the transmission rod 40 is surrounded—except at its farthest distal end—by an insulation sleeve 412 in mantle form that includes a collar 413 in its center area. At the farthest distal end, the distal portion 411 of the transmission rod 40 comprises two joints 415, 416. A first connection rod 256 connects the first joint 415 on the distal end of the transmission rod 40 with a joint 258 on the first jaw member 25 that is at a distance from the axle 232. A second connection rod 266 connects the second joint 416 on the distal end of the transmission rod 40 with a joint 268 on the second jaw member 26 that is at a distance from the axle 232. It is clear from a comparison of FIGS. 19 through 21 that a linear sliding of the transmission rod 40 parallel to the longitudinal axis 29 of the tool 20 by means of the connection rods 256, 266 causes a pivoting of the jaw members 25, 26 around the joints formed by the axle 232.

The transmission rod 40 includes in addition a proximal portion 421 that extends particularly from the proximal end 42 of the transmission rod recognizable in FIG. 2 all the way to the proximal end of the distal portion 411 of the transmission rod 40. The proximal portion 421 of the transmission rod 40 is joined with the distal portion 411 of the transmission rod 40 by means of a connecting sheath 43—in particular in form-locked, force-locked or firmly bonded connection. The proximal portion 421 and the connecting sheath 43 are enclosed by an insulating mantle 422. The distal end of the insulating mantle 422 overlaps with the proximal end of the insulation sleeve 412 of the distal portion of the transmission rod 40.

The proximal portion 421 of the transmission rod 40 and the insulating mantle 422 are, in particular, of pliable and, with respect to longitudinal forces and torsion, rigid configuration. Because of the pliable configuration of the transmission rod 40, the transmission rod, even in a curved shaft 30, can be slid in the longitudinal direction and rotated around its longitudinal axis. Because of the rigid configuration of the transmission rod 40 with respect to longitudinal forces and torsion, the transmission rod can transmit forces and torque from the handling device shown in FIGS. 1 and 2 to the tool 20.

The tool 20 includes, in addition, a locking device 48. The locking device 48 includes a ring-shaped portion 480 and several bolts configured as convex sections on the locking device 48. The ring-shaped portion 480 and the bolts 484 are, in particular, configured as single pieces. The ring-shaped portion 480 of the locking unit 48 encloses the distal portion 411 and the insulation sleeve 412 of the transmission rod 40 directly proximal from the collar 413 on the insulation sleeve 412.

Proximally from the ring-shaped portion 480 of the locking device 48, a ring 44 encloses the insulation sleeve 412 and the distal portion 411 of the transmission rod 40. The ring 44 is arranged so that between the collar 413 of the insulation sleeve 412 and the ring 44, a groove is situated that surrounds the transmission rod 40 in ring shape and in which the ring-shaped portion 480 of the locking device 48 is guided with little play or friction. The locking device 48 can thus rotate around the longitudinal axis 29 of the tool 20, but is guided precisely in axial direction. Axial movements of the transmission rod 40, which can be recognized in comparing FIGS. 19 through 21, are transposed precisely into corresponding axial movements of the locking device 48.

The bolts 484 on the locking device 48 each engage in an axial portion of a T-shaped slot 274 in the connecting component 27. Thus the locking device 48 is guided with respect to a rotation around the longitudinal axis 29 of the tool 20 by the axial portions of the T-shaped slots 274 in the connecting component 27 in which the bolts 484 engage, and with respect to an axial movement parallel to the longitudinal axis 29 of the tool 20 by the surrounding ring-shaped groove between the collar 413 on the insulating sleeve 412 and the ring 44 in which the ring-shaped portion 480 of the locking device 48 engages.

Axial sliding of the transmission rod 40 parallel to the axis 29 of the tool 20, as can be recognized in comparing FIGS. 19 through 21, thus leads to a corresponding slide of the locking device 48. In particular the locking device 48 is situated in the installation position 483 shown in FIG. 19 when the jaw members 25, 26 are in their fully open positions 253, 263 shown in FIG. 19. The locking device 48 is situated in a first working position 481 when the jaw members 25, 26 are in their closed positions 251, 261. The locking device 48 is in a second working position 482 when the jaw members 25, 26 are in their open positions 252, 262. In all positions 481, 482, 483 of the locking device 48, the transmission rod 40 and with it the articulated device 23 and jaw members 25, 26 are rotated freely in relation to the connecting component 27 and shaft 30 around the longitudinal axis 29 of the tool 20.

Presented below, with reference to FIGS. 22 through 25, is a locking effect of bolts 484 of the locking device 48 on a mechanical connection or coupling of the tool 20 with the distal end 31 of a shaft 30. The mechanical connection or coupling between the tool 20 and the shaft 30 occurs by means of the T-shaped slot in the proximal area of the connecting component 27 and the bracket 36 on the distal end of the shaft 30. In FIGS. 22 through 25, therefore, only the connecting component 27, the distal end of the shaft 30 with the bracket 36, and the transmission rod 40 with the locking device 48 are shown.

Shown at the left in each of FIGS. 22 through 25 are a section along a plane A-A perpendicular to the longitudinal axis 29 of the tool 20 (see also FIGS. 19 through 21) and, in the right in each case, two overhead views of the connecting component 27, the distal end of the shaft 30 and the transmission rod 40. The planes of projection of the depictions at the right in FIGS. 22 through 25 are each perpendicular to the sectional plane A-A, parallel to the longitudinal axis 29 of the tool 20 (compare FIGS. 19 through 21) and perpendicular to the sectional planes and planes of projection of FIGS. 19 through 21. The position of the sectional plane A-A is indicated to the right in each of FIGS. 22 through 25.

The overhead views of the connecting component 27, the distal end of the shaft 30 and the transmission rod 40 are shown twice, one above the other, to the right in each of FIGS. 22 through 25. Shown above in each case are the contours of the connecting component 27 in continuous line, while the transmission rod 40, as long as it runs inside the connecting component 27 or the shaft 30, is shown only in broken lines. Shown below in each case is the transmission rod 40—as long as it is not positioned inside the shaft 30—in broken lines, and the connecting component 27 is indicated merely with non-contoured hatching.

In FIGS. 22 through 25 the T-shaped form of one slot 274 in each case can be recognized in the proximal area of the connecting component 27. The connecting component 27 includes in particular two T-shaped slots 274, which are displaced by 180 degrees with respect to one another on the basis of the longitudinal axis 29 of the tool 20 (compare FIGS. 19 through 21). Each T-shaped slot in the connecting component 27 includes an axial portion with a distal area 275 and a proximal area 276 and a peripheral portion 277. The axial portion 275, 276 extends in the axial direction. The area situated distally from the outlet of the peripheral portion 277 into the axial portion of the T-shaped slot 274 is designated as the distal area 275 of the axial portion of the T-shaped slot 274. The area situated proximally from the outlet of the peripheral portion 277 into the axial portion of the T-shaped slot 274 is designated as the proximal area 276 of the axial portion of the T-shaped slot 274.

Also recognizable in FIGS. 22 through 25, but not in FIGS. 19 through 21, is the aforementioned axial slot 278 on the connecting component 27, which extends in the axial direction starting from the distal border 271 of the connecting component 27. The collar 273 on the distal border 271 of the connecting component 27 is, in particular, interrupted by several axial slots 278, for example by four or six slots. The slots 278 make possible an elastic reshaping of the connecting component 27 at its distal end upon insertion into the articulated device 23 to the point of engaging the collar 273 in the groove 237 on the articulated device 23 (compare FIGS. 19 through 21). The supporting sheath 281 shown in FIGS. 19 through 21, which holds the collar 273 after the installation in the surrounding groove 237, is not shown in FIGS. 22 through 25.

Figure 22:
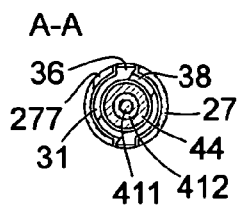
FIG. 22 shows a schematic depiction of coupling devices.
Figure 22:
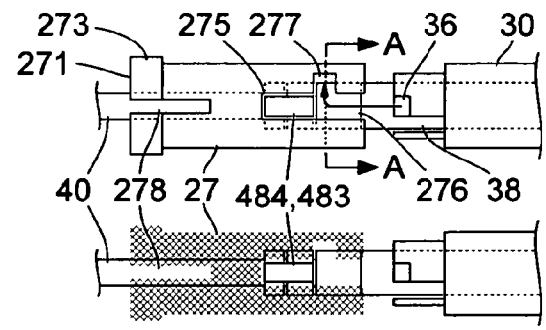
Figure 23:
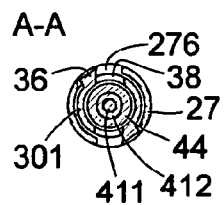
FIG. 23 shows another schematic depiction of the coupling devices from FIG. 22.
Figure 23:
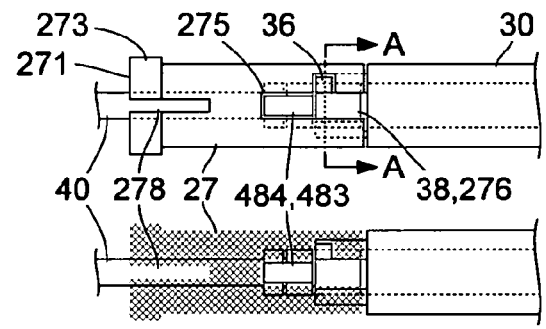
Figure 24:
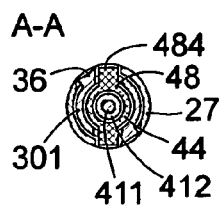
FIG. 24 shows another schematic depiction of the coupling devices from FIGS. 22 and 23.
Figure 24:
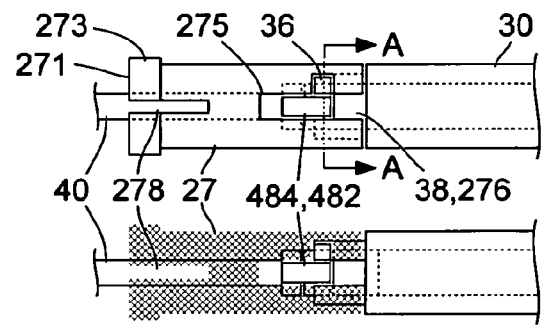
Figure 25:
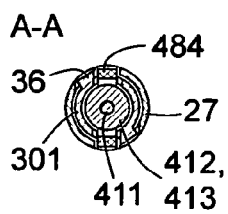
FIG. 25 shows another schematic depiction of the coupling devices from FIGS. 22 through 24.
Figure 25:
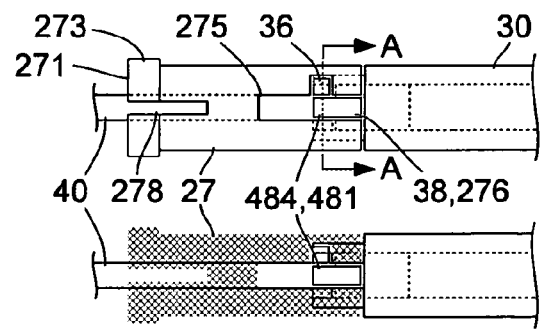

Also recognizable in FIGS. 22 through 25 is an axial slot 38 on the distal end of the shaft 30 whose functioning is described below, in particular with reference to FIGS. 24 and 25.

In the situations illustrated in FIGS. 22 and 23, the locking device 48 is situated in the installation position 483 also shown in FIG. 19. The bolt 484 engages exclusively in the distal area 275 of the axial portion of the T-shaped slot 274. The bracket 36, as indicated in FIG. 22 by an arrow, can be moved into the peripheral portion 277 of the T-shaped slot 274 through the proximal area 276 by an axial movement followed by a rotary movement of the shaft 30 in relation to the connecting component 27.

In the situations illustrated in FIGS. 23, 24 and 25, the bracket 36 is situated in the peripheral portion 277 of the T-shaped slot 274. If the bracket 36 is situated in the peripheral portion 277 of the T-shaped slot 274, a mechanical connection is formed between the connecting component 27 and the distal end of the shaft 30 by form-locking between the bracket 36 and the peripheral portion 277 of the T-shaped slot 274. Thus a form-locked connection between the entire tool 20 and the shaft 30 is also formed that, in particular, accepts tractive forces. The T-shaped slot 274 on the connecting component 27 and the brackets 36 on the distal border of the metallic tube 301 thus form coupling devices or are components of coupling devices for detachable mechanical coupling of the connecting component 27 with the distal end 31 of the shaft 30.

As long as the locking device 48, as shown in FIGS. 22 and 23, is situated in the installation position 483, which is also shown in FIG. 19, the bracket 36 can be removed again from the T-shaped slot 274 in the connecting component 27 by a rotary movement and then an axial movement of the shaft 30 in relation to the connecting component 27.

In the situation shown in FIG. 24, the locking device 48 is situated in the second working position 482, which is also shown in FIG. 20. In the situation shown in FIG. 25 the locking device 48 is situated in the first working position 481, also shown in FIG. 21. Both in the first working position 481 and in the second working position 482 of the locking device 48, the locking device 48 engages in the radial direction through the slot 38 on the distal end of the shaft 30. In particular, the bolt 484 engages through the slot 38 radially outward.

In both working positions 481, 482 of the locking device 48, the bolt 484 of the locking device 48 is no longer exclusively in the distal area 275 of the T-shaped slot 274, but rather at least partly in the area of the outlet of the peripheral portion 277 of the T-shaped slot 274 into the axial portion 275, 276. Thus the bolt 484 holds or blocks the bracket 36 in the peripheral portion 277 of the T-shaped slot 274. The locking device 48, in particular the bolt 484, in the working positions 481, 482 shown in FIGS. 20, 21, 24 and 25, thereby locks the mechanical connection or coupling of the tool 20 with the distal end of the shaft 30.

The structure of the tool 20 as shown in FIGS. 19 through 21 is suited for a bipolar micro-invasive surgical instrument with which a high-frequency alternative current is applied between the jaw members 25, 26 in order to atrophy tissue gripped or severed by the jaw members 25, 26 with a flow of current, in particular to coagulate protein. The contacting of the jaw members 25, 26 or the application of electric current and electric power to the jaw members 25, 26 is described below with reference to FIGS. 26 and 27.

Figure 26:
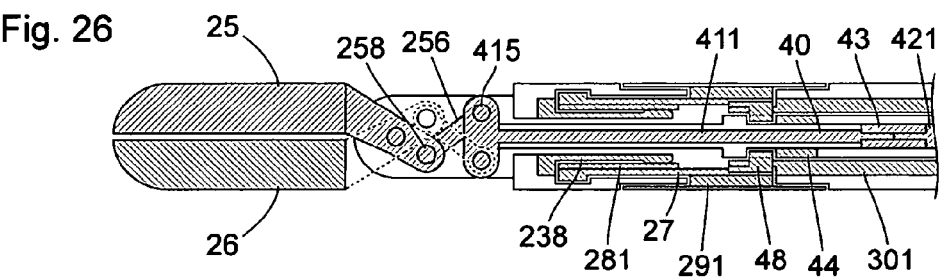
FIG. 26 shows another schematic depiction of the tool from FIGS. 19 through 21.
Figure 27:
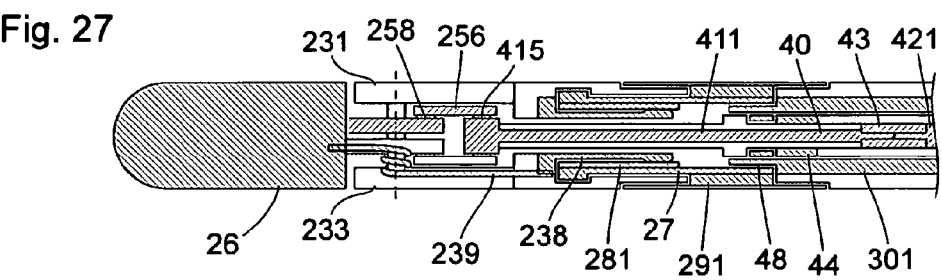
FIG. 27 shows another schematic depiction of the tool from FIGS. 19 through 21 and 26.

The tool 20 with the distal end 31 of the shaft 30 is shown in schematic sectional depictions in FIGS. 26 and 27. The sectional plane of FIG. 26 corresponds to the sectional planes of FIGS. 19 through 21. The sectional plane of FIG. 27 is perpendicular to the sectional planes of FIGS. 19 through 21 and 26, parallel to the planes of projection of the depictions shown in the right in FIGS. 22 through 25 and parallel to the longitudinal axis 29 of the tool 20.

All electrically conductive elements that are connected electrically conductively with the first jaw member 25 are indicated with hatching from below left to above right in FIGS. 26 and 27. All elements that are electrically conductively connected with the second jaw member 26 are shown with hatching from below right to above left. Elements that comprise electrically insulating materials are, like hollow spaces, not indicated with hatching and—apart from the blades 231, 233—not provided with reference numbers. To display the electrically conductive connection to the jaw members, in particular to the second jaw member 26, FIG. 27 departs from a sectional depiction in the area to the left of the center of the image or distally from the joints 415, 416 on the distal end of the transmission rod 40. In this distal area, FIG. 27 corresponds to an overhead view.

The first jaw member 25 is electrically contacted via the proximal portion 421 of the transmission rod 40, the connecting sheath 43, the distal portion 411 of the transmission rod 40, the joint 415, the first connection rod 256 and the joint 258 on the first jaw member 25. The second jaw member 26 is contacted by the metallic tube 301 of the shaft 30, the bracket 36 that is situated in neither of the two sectional planes of FIGS. 26 and 27 (compare FIGS. 19 and 22 through 25), the locking device 48, the connecting component 27, the supporting sheath 281, the contact component 238 and an elastic, electrically conductive component 239 shown only in FIG. 27.

The elastic electrically conductive component 239 is formed especially by a metallic wire that has a helical portion at the axle 232. The proximal end of the elastic electrically conductive component 239 is connected with the distal end of the contact component 238, for example plugged in, clamped, welded or soldered. In particular, the proximal end of the elastic electrically conductive component 239, contrary to the depiction in FIG. 27, is plugged into the lumen of a tube that has been soldered or welded with the contact component 238. A slight curvature of the proximal end of the elastic electrically conductive component 239 can cause an elastic clamping of the proximal end of the elastic electrically conductive component 239 in the tube and thus a reliable contact. The distal end of the elastic electrically conductive component 239 is electrically conductively connected with the second jaw member 26, for example clamped, plugged in, soldered or welded.

The proximal portion of the elastic electrically conductive component 239 is, in particular, positioned in one of the blades 231, 233 of the articulated device 23. A distal portion of the elastic electrically conductive component 239 is situated, in particular, in an electrically insulating portion of the second jaw member 26, which includes the bearing on the axle 232 and the joint 268 to the second connection rod 266.

In the embodiments presented above, the transmission rod 40 is configured both to transmit a translational movement in a direction parallel to the shaft 30 or to its longitudinal axis and to a corresponding pulling and/or pushing force, and to transmit a rotational movement and a corresponding torque to the tool 20. Contrary to the explanation with reference to the drawings, the tool 20 on the distal end 31 of the shaft 30 can be rotatable merely around the longitudinal axis of the distal end 31 of the shaft 30 or around another axis. For example, the tool 20 includes a finger-shaped or other manipulator or an electrode in hook or loop form or in another shape. In this case, a configuration of the transmission rod 40 to transmit a translational movement in a direction parallel to the shaft 30 and to transmit a corresponding force is required only to the extent that it is necessary for moving the locking device 48. Alternatively, a finger-shaped or other manipulator or an electrode in hooked or loped form or in another shape can be not only rotated but also in addition can be movable by means of a longitudinal movement of the transmission rod 40 parallel to the shaft 30 or to its longitudinal axis. For example, a hook-shaped manipulator is configured, in a movement essentially parallel to the longitudinal axis of the shaft 30 in the proximal direction, to clamp an object between the hook-shaped manipulator and a portion of the tool that is not slidable in the longitudinal direction.

What is claimed is:

1. A tool that is adapted to be detachably mechanically coupled with a distal end of a shaft for a micro-invasive surgical instrument, having:
    an articulated device to which a jaw member or other active device is attached;
    a connecting component that is mechanically connected to rotate with the articulated device, and which comprises a coupling device for detachable mechanical coupling with a distal end of a shaft;
    a transmission rod to transmit at least either a force or a torque from a proximal end of a shaft that is detachably mechanically coupled with the tool to the jaw member or to the other active device, and
    a locking device that is mechanically coupled with the transmission rod in such a way that the locking device is rotatable in relation to the transmission rod but is not axially slidable in relation to the transmission rod, such that the locking device is mechanically mounted in the connecting component in such a way that the locking device is slidable axially in relation to the connecting component but is not rotatable in relation to the connecting component, wherein the locking device includes a ring-shaped portion that engages in a surrounding groove on the transmission rod.

2. The tool according to claim 1, wherein:
    the locking device is slidable in axial direction between an installation position and a working position, such that with the locking device in the installation position the connecting component is adapted to connect with a distal end of a shaft and detach from the locking device, such that with the locking device in the working position a mechanical connection of the tool with a distal end of a shaft is locked.

3. The tool according to claim 1, wherein the locking device includes at least either an electrically insulating material or is electrically insulated from the transmission rod.

4. The tool according to claim 1, wherein the articulated device includes an electrically insulating material, and an electrically conductive conducting component that is positioned at least partly in the articulated device for electrical contacting of a jaw member or other active device that is electrically insulated from the transmission rod.

5. The tool according to claim 1, wherein
    the coupling device is configured as a bayonet coupling with a bracket,
    the locking device includes a convex portion,
    such that the bracket and the convex portion are at a distance from one another in the axial direction and in the peripheral direction and are configured to engage in a groove or a slot on a distal end of a shaft.

6. The tool according to claim 1, wherein the locking device is configured and positioned in order to hamper, in the working position, a rotation of the coupling device in relation to the distal end of the shaft by engaging in a portion of a groove or slot extending in an axial direction on a distal end of a shaft.

7. The tool according to claim 1, wherein the locking device engages in a groove or a slot on the coupling device configured as a bayonet coupling.

8. The tool according to claim 7, wherein
    the groove or slot comprises a T-shaped form with an axial portion that extends in an axial direction and with a peripheral portion extending in a peripheral direction, such that a proximal area of the axial portion is positioned proximally from an outlet of the peripheral portion into the axial portion and such that a distal area of the axial portion is positioned distally from an outlet of the peripheral portion into the axial portion;
    the locking device in installation position engages only in the distal area of the axial portion of the groove or slot, so that a bracket on a shaft that is to be connected with the tool is insertable through the proximal area of the axial portion into the peripheral portion of the groove or slot;
    the locking device in the working position at least partly blocks the outlet of the peripheral portion of the groove or slot into the axial portion, so that a bracket positioned in the peripheral portion of the groove or slot is held on a shaft that is connected with the tool by the locking device in the peripheral portion.

9. The tool according to claim 1, wherein
    the jaw member is electrically insulated from another jaw member;
    the other jaw member is electrically conductively connected with a contact component that is mechanically rigidly connected with the articulated device;
    a proximal front surface of the contact component is contiguous with a contact surface that is mechanically rigidly connected with the connecting component;
    the contact component and the contact surface that is mechanically rigidly connected with the connecting component are configured in order to form an electrically conductive connection between a shaft connected with the tool and the other jaw member.

10. The tool according to claim 1, wherein the connecting component comprises close to its distal end a collar that is interrupted by several essentially axial slots and engages in a corresponding groove on the articulated device, in addition having:
    a supporting device that is configured to hamper a radial reshaping of the collar and to hold the collar in the groove.

11. The tool according to claim 10, wherein the supporting device is configured as a supporting sheath, and further includes
    a contact component with a contact surface that is contiguous with the supporting sheath, such that the contact component is configured and positioned to be rotatable together with the articulated device with respect to the connecting component.

12. The tool according to claim 1, wherein the jaw member is curved.

13. A micro-invasive surgical instrument comprising:
a shaft with a proximal end that is coupleable with a handling device, and a distal end; and
a tool according to claim 1, wherein said tool is adapted to be detachably mechanically coupled with the distal end of the shaft.

14. The micro-invasive surgical instrument according to claim 13, wherein the distal end of the shaft comprises a bayonet coupling area with an L-shaped groove or an L-shaped slot.

* * * * *